(12) United States Patent
Ran

(10) Patent No.: US 10,494,341 B2
(45) Date of Patent: Dec. 3, 2019

(54) COMPOUND CONTAINING INDOLEACETIC ACID CORE STRUCTURE AND USE THEREOF

(71) Applicant: Beijing An Jian Xi Bio-Medical Technology Co., Ltd., Beijing (CN)

(72) Inventor: Ruiqiong Ran, Hubei Province (CN)

(73) Assignee: Beijing An Jian Xi Bio-Medical Technology Co., Ltd., Beijing (CN)

( * ) Notice: Subject to any disclaimer, the term of this patent is extended or adjusted under 35 U.S.C. 154(b) by 62 days.

(21) Appl. No.: 15/547,013

(22) PCT Filed: Jan. 25, 2016

(86) PCT No.: PCT/CN2016/071934
§ 371 (c)(1),
(2) Date: Jul. 27, 2017

(87) PCT Pub. No.: WO2016/119643
PCT Pub. Date: Aug. 4, 2016

(65) Prior Publication Data
US 2018/0022700 A1 Jan. 25, 2018

(30) Foreign Application Priority Data
Jan. 27, 2015 (CN) .......................... 2015 1 0040470

(51) Int. Cl.
| | | |
|---|---|---|
| *C07D 209/26* | (2006.01) |
| *A61K 31/216* | (2006.01) |
| *A61K 31/405* | (2006.01) |
| *C07C 317/44* | (2006.01) |
| *A61K 9/00* | (2006.01) |
| *A61K 31/337* | (2006.01) |
| *A61K 31/635* | (2006.01) |
| *A61K 31/661* | (2006.01) |
| *A61K 31/704* | (2006.01) |
| *A61K 45/06* | (2006.01) |

(52) U.S. Cl.
CPC .......... *C07D 209/26* (2013.01); *A61K 9/0019* (2013.01); *A61K 9/0053* (2013.01); *A61K 31/216* (2013.01); *A61K 31/337* (2013.01); *A61K 31/405* (2013.01); *A61K 31/635* (2013.01); *A61K 31/661* (2013.01); *A61K 31/704* (2013.01); *A61K 45/06* (2013.01); *C07C 317/44* (2013.01); *C07C 2602/08* (2017.05)

(58) Field of Classification Search
CPC .................................................. C07D 209/26
See application file for complete search history.

(56) References Cited

U.S. PATENT DOCUMENTS 3,654,349 A    4/1972 Shen et al.

FOREIGN PATENT DOCUMENTS

| CN | 1237162 | 12/1999 |
| CN | 104592091 | 5/2015 |
| WO | WO 2006099416 | 9/2006 |

OTHER PUBLICATIONS

Vippagunta, et al. Advanced Drug Delivery Reviews 48, Mar. 26, 2001.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*

* cited by examiner

*Primary Examiner* — Shawquia Jackson
(74) *Attorney, Agent, or Firm* — IP & T Group LLP

(57) ABSTRACT

Disclosed are a compound as shown by the following formula 1, and a pharmaceutically acceptable salt, an ester, a hydrate and an organic solvate thereof. In the formula (1), the groups $R_1$ to $R_{17}$ are independently selected from the group consisting of hydrogen, fluorine, chlorine, bromine, iodine, $C_1$-$C_8$ alkyl, $C_1$-$C_8$ alkoxy, carbonyl, hydroxyl, amino, azido, carboxyl and $C_1$-$C_8$ alkylsulfinyl, respectively; and X is a carbon or nitrogen atom; Y is selected from the following groups: a single bond, $C_1$-$C_8$ alkylene, $C_6$-$C_{20}$ arylene and $C_4$-$C_{20}$ heteroarylene; and n is an integer from 5 to 20. Also provided in the present invention are a pharmaceutical composition containing the compound, and use thereof in the field of tumor therapy.

Formula (1)

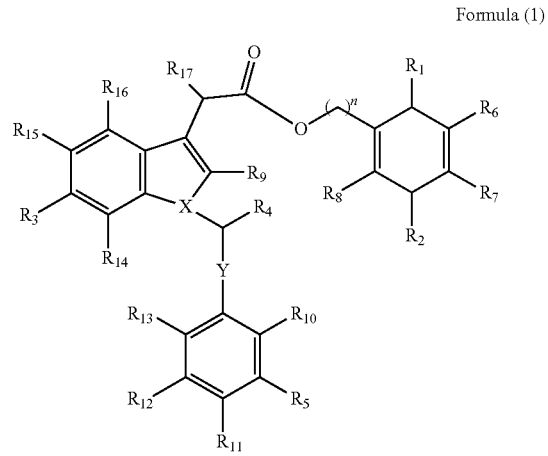

4 Claims, 8 Drawing Sheets

COMPOUND CONTAINING INDOLEACETIC ACID CORE STRUCTURE AND USE THEREOF

This application is a national stage application of PCT/CN2016/071934 filed on Jan. 25, 2016, which claims priority of Chinese patent application number 201510040470.5 filed on Jan. 27, 2015. The disclosure of each of the foregoing applications is incorporated herein by reference in its entirety.

TECHNICAL FIELD

The present invention belongs to the field of medicine and pharmaceutical chemistry, and relates to a compound for improving the sensitivity of tumor to treatment and reducing the side effects of radiotherapy and chemotherapy for malignant tumor, and its preparation and use. Specifically, the present invention provides a compound containing indoleacetic acid core structure and the use thereof for improving the sensitivity of tumor to treatment and reducing the side effects of radiotherapy and chemotherapy for malignant tumor.

BACKGROUND ART

Chemotherapy and radiotherapy are the primary treatment means for cancers. However, the two treatment means face a common challenge in clinical practice, i.e. treatment-induced side effects and insensitivity of tumor to treatment. Since the two treatment methods lack selectivity among normal cells and cancer cells and result in damage of normal cells and produce side effects, patients often die of complications induced by radiotherapy and chemotherapy, and the survivors' life quality is also very poor. In addition, the adverse effects always limit the therapeutic dose, and greatly affect the therapeutic effect.

Based on the current status and the present bottleneck of the field of therapy against tumor, the clinical use of cytoprotective agents and the development of targeted anti-cancer drugs seem to partially alleviate the side effects of treatment to a certain extent in recent years. However, clinical data confirmed that the new generations of targeted anti-cancer drugs still have two major drawbacks: 1. patients are prone to tolerance to the treatment; 2. targeted anti-cancer drugs are expensive and narrow in indications. Therefore, traditional treatment means still dominate for about 95% of patients with tumor. The commercially-available cytoprotective agents such as amifostine are very narrow in indications, and they have significant interference with therapeutic effects. Traditional antioxidants such as glutathione and Vit-E have been proven to be ineffective clinically.

Another difficult problem is that the tumor cells will produce tolerance in the process of treatment. The existing radiotherapy sensitizers, such as sodium glycididazole, are only suitable for radiation-sensitized therapy of a part of tumors, and they have a narrow range of indications and multiple contraindications. Moreover, they have evident cardiac toxicity as well as the drawback of promoting oxidative damage of normal tissues.

Existing products either only have a sensitizing effect or only have the function of reducing side effects, so there is a clinical need to develop a new drug that can alleviate side effects while enhance the sensitivity of tumors to treatment. The source of resistance of tumors to treatment lies in the overactivity of enzymes associated with proliferation. It has been found in studies that overexpression of COX2 by tumor cells is one of the causes for the resistance of tumors to treatment, and inhibition of COX2 expression can restore the sensitivity of the tumors to the treatment to a certain extent. However, clinical experimental results have shown that the side effects on cardiovascular system induced by COX2 inhibitors limit the use thereof although selective COX2 inhibitors have certain sensitizing effect. The inventor has found in the latest study that COX1 activity is actually the key factor that determines whether the tumor cells are sensitive to treatment. That is to say, the purpose of enhancing the sensitivity of tumors to treatment at the greatest extent can only be achieved truly by inhibiting COX1 and COX2 at the same time. However, the existing drugs that can inhibit both COX1 and COX2 at the same time will lead to a strong side effect of gastrointestinal bleeding and a certain degree of hepatotoxicity, greatly restricting its practical application. Accordingly, there is an urgent need in the art for the development of a novel drug capable of simultaneously inhibiting COX1 and COX2 and overcoming the above-mentioned gastrointestinal irritation and hepatotoxicity.

In addition, drugs against oxidative injury are often used in the meantime during the process of cancer treatment to relieve the treatment-induced side effects. However, due to the first pass effect of liver, the bioavailability for oral administration of some conventional drugs against oxidative injury is poor, and thus the in vivo anti-oxidant effect thereof is unsatisfactory. It is also highly desirable to develop drugs which have a high bioavailability and can maintain their effect of alleviating side effects.

A novel compound is developed in the present invention, and it effectively solves the two bottlenecks that the treatment of tumors faces, i.e. treatment resistance (tolerance) and side effect. Specifically, the compound developed by the present invention does not induce significant gastrointestinal irritation, it can avoid hepatotoxicity, and at the same time have excellent tumor-sensitizing effect and the effect of protecting normal cells from side effects of cancer treatment. The inventors performed experimental treatments on mice with colon cancer using the compound. The results show that the volume of tumor in the mice administrated with the compound is significantly decreased and that the damage of normal tissues is greatly reduced.

In addition, the applicant has also found that the compound of the present invention can be used as a medicament for treating a tumor, and used alone or in combination with other drugs for treatment of tumors and can achieve the effect of inhibiting tumor cell proliferation or killing tumor cells.

SUMMARY OF THE INVENTION

The first aspect of the present invention provides a compound of the formula 1:

Formula (1)

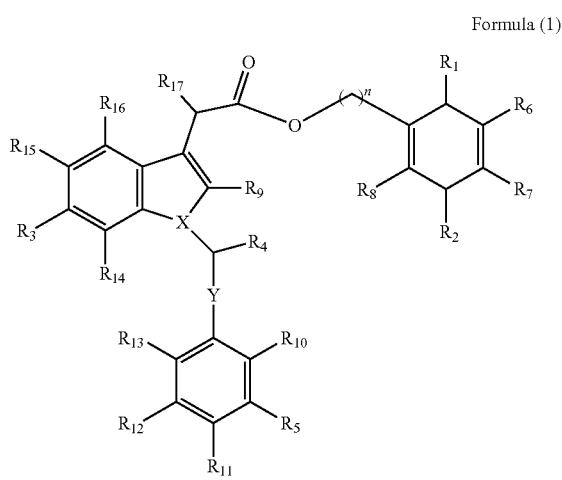

wherein, the groups $R_1$ to $R_{17}$ are each independently selected from the group consisting of hydrogen, fluorine, chlorine, bromine, iodine, $C_1$-$C_8$ alkyl, $C_1$-$C_8$ alkoxy, carbonyl, hydroxyl, amino, azido, carboxyl and $C_1$-$C_8$ alkylsulfinyl; X is a carbon atom or a nitrogen atom; Y is selected from the group consisting of single bond, $C_1$-$C_8$ alkylene, $C_6$-$C_{20}$ arylene and $C_4$-$C_{20}$ heteroarylene; n is an integer from 5 to 20, and a pharmaceutically acceptable salt, ester, hydrate, and organic solvate thereof. In a preferred embodiment, the groups $R_1$ to $R_4$ are each independently selected from the group consisting of hydrogen, fluorine, chlorine, $C_1$-$C_4$ alkyl, $C_1$-$C_4$ alkoxy, carbonyl and hydroxyl; $R_{11}$ is selected from the group consisting of hydrogen, fluorine, chlorine, bromine, iodine, azido and $C_1$-$C_3$ alkylsulfinyl; $R_6$ to $R_9$ are each independently selected from hydrogen, $C_1$-$C_4$ alkyl and $C_1$-$C_4$ alkoxy; $R_5$, $R_{10}$, $R_{12}$ to $R_{17}$ are each independently selected from hydrogen, $C_1$-$C_4$ alkyl, $C_1$-$C_4$ alkoxy and amino; X is a carbon atom or a nitrogen atom; Y is selected from the group consisting of single bond, $C_1$-$C_6$ alkylene, $C_6$-$C_{15}$ arylene and $C_4$-$C_{15}$ heteroarylene; n is an integer of 5 to 20, preferably n=10.

The linking relationship of the atoms is clearly defined in the formula (1) of the present invention, and some atoms are omitted according to the general practice for drawing chemical structures. For example, hydrogen atoms attached to carbon are omitted from the group ⤳, , and such omissions belong to common knowledge in the art. With the change of the atomic species in the formula (1), those skilled in the art can clearly and unambiguously determine the atoms and the connection modes omitted in the formula.

Specifically, when X is a carbon atom and $R_4$ is a monovalent group, a double bond is necessarily formed between X and the carbon atom linking with X, $R_4$ and Y at the same time, as shown in the following formula:

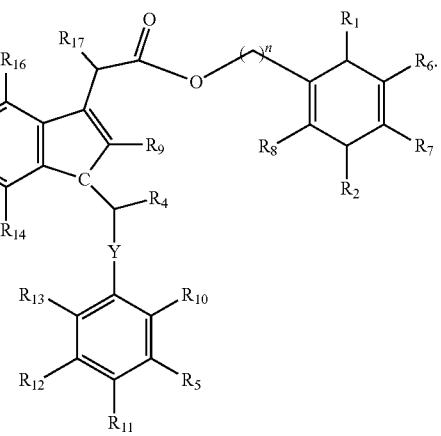

When X is a nitrogen atom and $R_4$ is a monovalent group, a single bond is necessarily formed between X and the carbon atom linking with X, $R_4$ and Y at the same time, as shown in the following formula:

In the present invention, "$R_4$ is carbonyl" means that $R_4$, as the oxygen atom of carbonyl, forms carbonyl together with the carbon atom to which it is linked.

Specifically, when X is a nitrogen atom and $R_4$ is carbonyl, the compound of the formula (1) has the following structure:

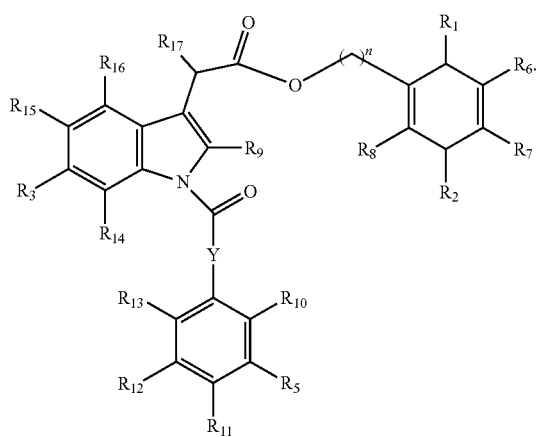

In a more preferred embodiment of the present invention, the compound is selected from the compounds shown any of the following formulae a to f, and pharmaceutically acceptable salts, esters, hydrates and organic solvates thereof:

a
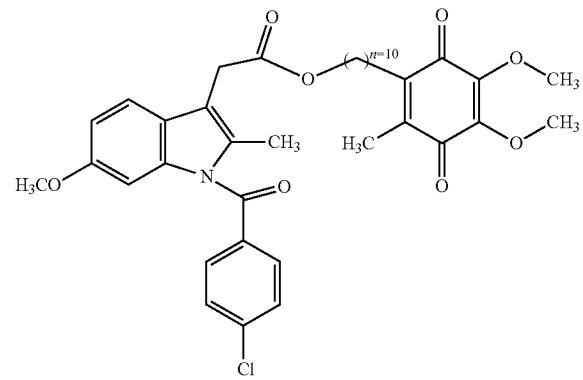

b
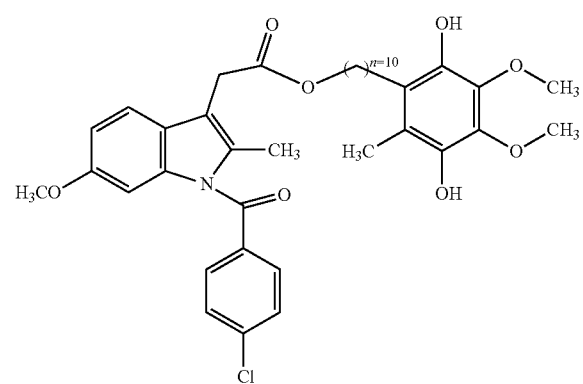

c
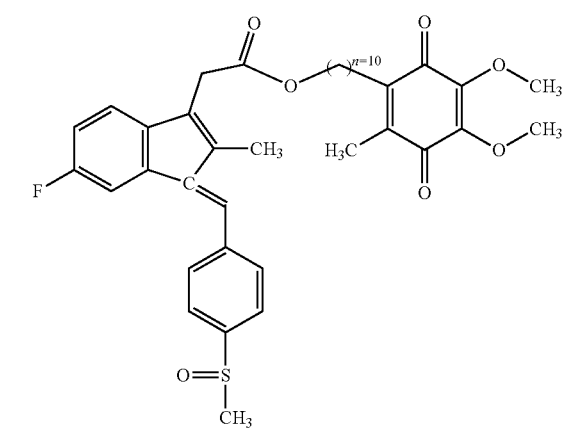

d
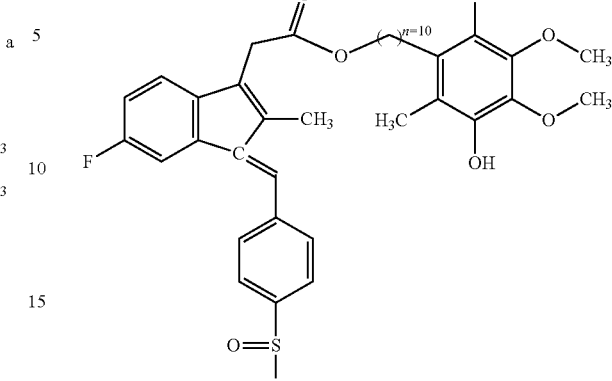

e
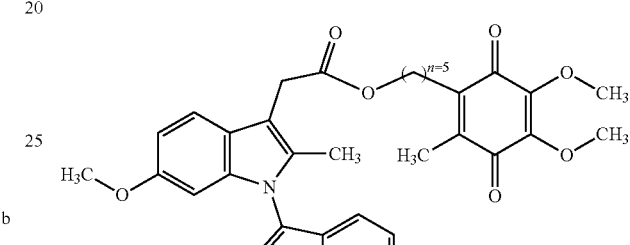

f
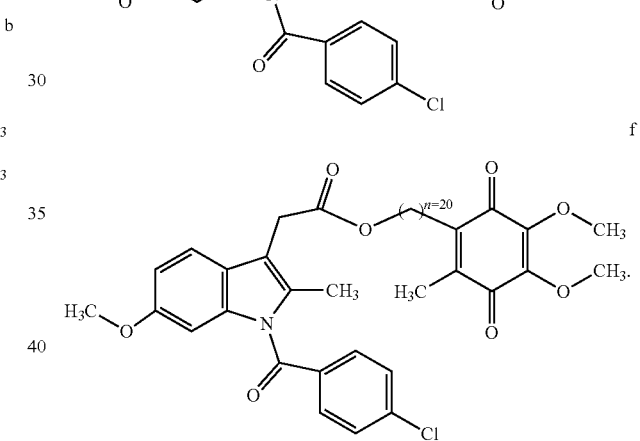

The second aspect of the present invention provides a pharmaceutical composition comprising: (i) the compound of the present invention as described above, or a pharmaceutically acceptable salt, ester, hydrate, organic solvate, prodrug, metabolic intermediate, and metabolite thereof; (ii) optionally one or more of pharmaceutically acceptable fillers, carriers and diluents; and (iii) optionally pharmaceutically active component different from the component (i). Preferably, the component (i) is selected from the group consisting of: one of the compounds of formulae a to d; a mixture of a compound of formula a and a compound of formula b; a mixture of a compound of formula a and a compound of formula c; a mixture of a compound of formula a and a compound of formula d; a mixture of a compound of formula a and a compound of formula e; a mixture of a compound of formula a and a compound of formula f; a mixture of a compound of formula b and a compound of formula c; a mixture of a compound of formula b and a compound of formula d; a mixture of a compound of formula b and a compound of formula e; a mixture of a compound of formula b and a compound of formula f; a mixture of a compound of formula c and a compound of formula d; a mixture of a compound of formula c and a compound of formula e; a mixture of a compound of formula c and a compound of formula f; a mixture of a compound of formula d and a compound of formula e; a mixture of a compound of formula d and a compound of formula f; a mixture of a compound of formula e and a compound of formula f; a mixture of a compound of formula a, a compound of formula b, and a compound of formula c; a mixture of a compound of formula a, a compound of formula c and a compound of formula d; a mixture of a compound of formula a, a compound of formula b and a compound of formula e; a mixture of a compound of formula a, a compound of formula b and a compound of formula f; a mixture of a compound of formula a, a compound of formula d and a compound of formula e; a mixture of a compound of formula a, a compound of formula d and a compound of formula f; a mixture of a compound of formula a, a compound of formula e and a compound of formula f; a mixture of a compound of formula b, a compound of formula c and a compound of formula d; a mixture of a compound of formula b, a compound of formula e and a compound of formula f; and a mixture of a compound of formula a, a compound of formula b, a compound of formula c and a compound of formula d. In a preferred embodiment of the invention, said (iii) optionally a pharmaceutically active component different from the component (i) is selected from one or more of the following substances: uramastine, amifostine, chlorambucil, mustine, cyclophosphamide, paclitaxel, Thiotepa, cisplatin, busulfan, doxorubicin, carmustine, 5-fluorouracil, celecoxib, mercaptopurine, methotrexate, tegafur, gefitinib, hydroxyurea, cytosine arabinoside, carboplatin, Iproplatin, prednisone, prednisolone, dexamethasone, diethylstilbestrol, estradiol, raloxifene, Testosterone propionate, semustine, lomustine, thioguanine, etoposide, vincristine, ifosfamide, Navelbine, gemcitabine, mitomycin and vindesine.

The third aspect of the present invention relates to the use of the compound and a pharmaceutically acceptable salt, ester, hydrate and organic solvate thereof according to the invention, or a composition according to the invention, in the manufacture of a medicament for enhancing the sensitivity of tumors to treatment. Preferably, the medicament is an oral medicament. Alternatively, the medicament may be administered by one or more of oral administration, intravenous administration, percutaneous absorption, mucosal absorption and in vivo implantation.

The fourth aspect of the present invention relates to the use of the compound of the present invention, or a pharmaceutically acceptable salt, ester, hydrate or organic solvate thereof, or a composition according to the invention, in the manufacture of a medicament for reducing toxic and side effects of radiotherapy and chemotherapy for malignant tumor. Preferably, the medicament is an oral medicament. Alternatively, the medicament may be administered by one or more of oral administration, intravenous administration, percutaneous absorption, mucosal absorption and in vivo implantation.

The fifth aspect of the present invention relates to the use of the compound of the present invention, or a pharmaceutically acceptable salt, ester, hydrate or organic solvate thereof, or a composition according to the invention, in the manufacture of a medicament for the treatment of inflammatory diseases and degenerative diseases. Preferably, the medicament is an oral medicament. Alternatively, the medicament may be administered by one or more of oral administration, intravenous administration, percutaneous absorption, mucosal absorption and in vivo implantation.

The sixth aspect of the present invention relates to the use of the compound of the present invention, or a pharmaceutically acceptable salt, ester, hydrate or organic solvate thereof, or a composition according to the invention, in the manufacture of a medicament for the treatment of tumor. Preferably, the medicament is an oral medicament. Alternatively, the medicament may be administered by one or more of oral administration, intravenous administration, percutaneous absorption, mucosal absorption and in vive implantation.

BRIEF DESCRIPTION OF THE DRAWINGS

The following specific description is provided to explain in more detail the technical solutions, features and objects of the present invention with reference to the figures, which are illustrated as follows.

BEST MODE OF THE INVENTION

Figure 1A:
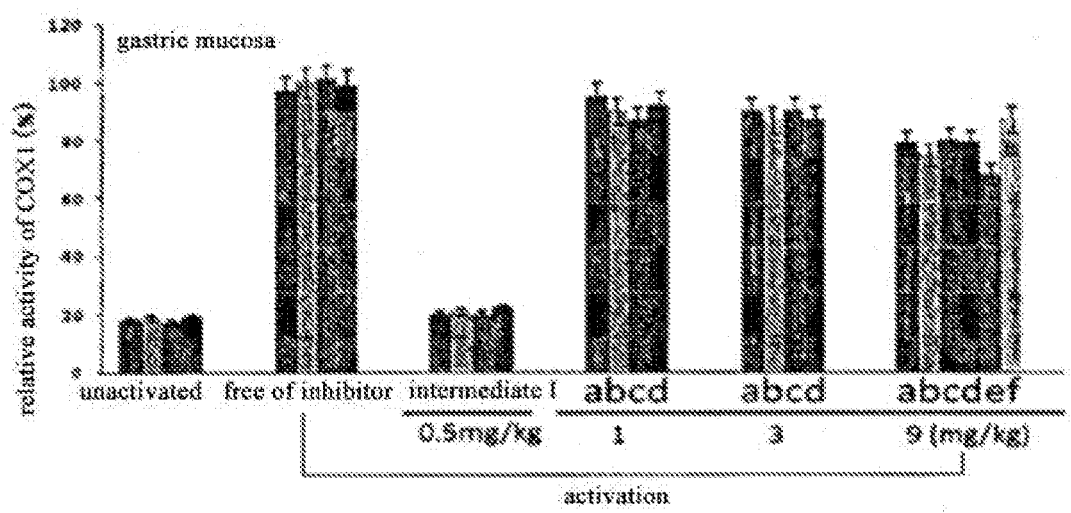
FIG. 1a shows the inhibitory effect of the compounds of the present invention on COX1 activity in gastric mucosa.

The present invention will be described below in further detail. It should be noted that the following specific embodiments only give specific operating examples of the present invention by exemplary way, but the protection scope of the present invention is not limited thereto. The scope of protection of the present invention is defined by the claims. It will be apparent to those skilled in the art that various other modifications and substitutions may be made to the embodiments described in the present invention within the scope as defined by the claims, and the modified or substituted embodiments can still realize the same technical effects and achieve the ultimate technical purpose of the present invention.

In the present invention, unless otherwise specified, all ratios are molar ratios or weight ratios, all percentages are calculated by weight, the unit of temperature is degree Celsius (° C.), and the unit of pressure is Pa. Room temperature refers to conventional ambient temperature in the laboratory, changes with season and location, and is usually 25° C. In addition, all numerical ranges described in the present invention include end values and may include new numerical ranges obtained by any combination of the upper and lower limits of the disclosed ranges.

The first aspect of the present invention provides a compound of the formula 1:

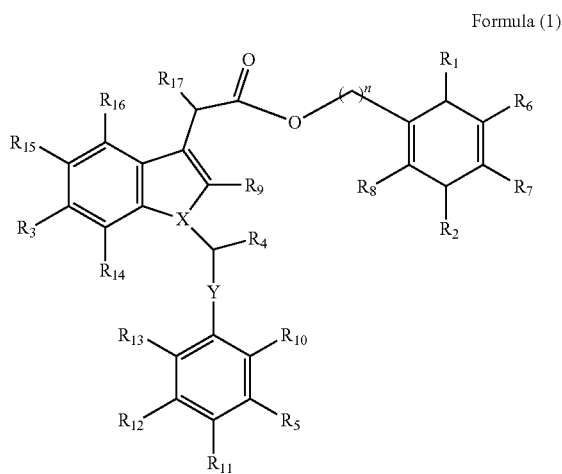

Formula (1)

wherein, the groups $R_1$ to $R_{17}$ are each independently selected from the group consisting of hydrogen, fluorine, chlorine, bromine, iodine, $C_1$-$C_8$ alkyl, $C_1$-$C_8$ alkoxy, carbonyl, hydroxyl, amino, azido, carboxyl and $C_1$-$C_8$ alkylsulfinyl; X is a carbon atom or a nitrogen atom; Y is selected from the group consisting of single bond, $C_1$-$C_8$ alkylene, $C_6$-$C_{20}$ arylene and $C_4$-$C_{20}$ heteroarylene; n is an integer from 5 to 20, and a pharmaceutically acceptable salt, an ester, a hydrate, and an organic solvate thereof. Preferably, the groups $R_1$ to $R_4$ are each independently selected from the group consisting of hydrogen, fluorine, chlorine, $C_1$-$C_4$ alkyl, $C_1$-$C_4$ alkoxy, carbonyl and hydroxyl; $R_{11}$ is selected from the group consisting of hydrogen, fluorine, chlorine, bromine, iodine, azido and $C_1$-$C_3$ alkylsulfinyl; $R_6$ to $R_9$ are each independently selected from hydrogen, $C_1$-$C_4$ alkyl and $C_1$-$C_4$ alkoxy; $R_5$, $R_{10}$, $R_{12}$ to $R_{17}$ are each independently selected from hydrogen, $C_1$-$C_4$ alkyl, $C_1$-$C_4$ alkoxy and amino; X is a carbon atom or a nitrogen atom; Y is selected from the group consisting of single bond, $C_1$-$C_6$ alkylene, $C_6$-$C_{15}$ arylene and $C_4$-$C_{15}$ heteroarylene; n is an integer of 5 to 20, more preferably n=10. More preferably, the compound is selected from the compounds of any of the above-mentioned formulae a to f, and pharmaceutically acceptable salts, esters, hydrates and organic solvates thereof.

In the present invention, the $C_1$-$C_8$ alkyl is selected from the group consisting of methyl, ethyl, n-propyl, isopropyl, n-butyl, sec-butyl, isobutyl, tert-butyl, n-pentyl, isopentyl, sec-pentyl, tert-pentyl, n-hexyl, isohexyl, sec-hexyl, t-hexyl, n-heptyl, isoheptyl, sec-heptyl, tert-heptyl, n-octyl, isooctyl, sec-octyl and tert-octyl. The $C_1$-$C_8$ alkoxy is a group in which any of the above alkyl groups is linked to a compound skeleton via an oxygen atom. The $C_1$-$C_8$ alkylene is selected from the group consisting of methylene, ethylene, n-propylene, isopropylene, n-butylene, sec-butylene, isobutylene, tert-butylene, n-pentylene, isopentylene, sec-pentylene, tert-pentylene, n-hexylene, isohexylene, sec-hexylene, tert-hexylene, n-heptylene, iso-heptylene, sec-heptylene, tert-heptylene, n-octylene, iso-octylene, sec-octylene and tert-octylene. The $C_6$-$C_{20}$ arylene is preferably selected from the group consisting of substituted or unsubstituted phenylene, substituted or unsubstituted naphthylene, substituted or unsubstituted anthrylene, substituted or unsubstituted biphenylene, substituted or unsubstituted binaphthylene, and the substituted arylene may be substituted with one or more groups selected from the group consisting of hydrogen, fluorine, chlorine, bromine, iodine, $C_1$-$C_8$ alkyl, $C_1$-$C_8$ alkoxy, carbonyl, hydroxyl, amino, azido, carboxyl and $C_1$-$C_8$ alkylsulfinyl. The $C_4$-$C_{20}$ heteroarylene represents a group in which any one or more carbon atoms in the aromatic ring of the above arylene are substituted with a heteroatom selected from N, O and S. In the present invention, when Y represents a "single bond", the carbon atom connected with $R_4$ is directly linked to the benzene ring at the lower part of the formula 1 without any middle group. For example, in the compound represented by formula a, $R_4$ represents =O, the carbon atom connected with the $R_4$ group is directly connected to the chlorophenyl group at the lower part, and here Y represents a single bond.

The compounds of the present invention can be administered to a patient during the radiotherapy and chemotherapy for cancer so as to selectively protect normal tissues and cells, to reduce the side effects induced by radiotherapy and chemotherapy, and to enhance the sensitivity of the tumor tissue to treatment. A high dose of the compound of the present invention can be administered as a chemotherapeutic agent to a patient suffered with tumor, and it significantly inhibit proliferation of the tumor. In general, the compounds of the present invention can be applied for the patients with any type of cancer. Examples of the cancer include but are not limited to liver cancer, gastric cancer, esophageal cancer, intestinal cancer, nasopharyngeal carcinoma, breast cancer, lymphoma, kidney cancer, pancreatic cancer, bladder cancer, ovarian cancer, uterine cancer, bone cancer, gallbladder cancer, lip cancer, melanoma, tongue cancer, laryngeal cancer, leukemia, prostate cancer, brain tumor and hemangioma. In fact, any patient receiving radiotherapy and chemotherapy can obtain reduced side effects of radiotherapy and chemotherapy and enhance the sensitivity of tumors to treatment by ingesting the compounds of the present invention.

The compounds of the present invention may be formulated into any dosage form and administered to a patient undergoing chemotherapy or radiotherapy in a suitable manner. For example, the compounds of the present invention may be formulated into solutions, suspensions, emulsions, tablets, capsules, pills, implants and other dosage forms, and administered to a patient by means of oral administration, intravenous injection, percutaneous absorption, mucosal absorption, in vivo implantation and others before, during or after radiotherapy and chemotherapy. The amount of the product of the present invention can be appropriately selected by a person skilled in the art depending on factors such as the type of disease of the patient, the physical condition, and the specific regimen of radiotherapy and chemotherapy. Daily doses can be administered once or more than once. In a preferred embodiment of the present invention, the preparation of the present invention is administered orally. For example, in one specific embodiment of the present invention, the compound of the present invention is orally administered twice daily, and the effective dose converted for a human is 1-5 mg/kg body weight/time. The inventors have found that when the compound of the present invention is administered 12-24 hours prior to anticancer drugs, most preferably 12 hours prior to anticancer drugs, the selectively protective effect on normal tissues and the inhibitory effect against tolerance of tumor cells can be greatly improved.

EXAMPLES

Some examples of the compound of the present invention are specifically described below in terms of synthesis, tests on biological functions and experimental treatments of tumors, but it is to be understood that the protection scope of the present invention is not limited to these examples.

Unless otherwise indicated, all of the chemical reagents used in the following synthesis examples are analytical-grade reagents purchased from Sigma-Aldrich. The water used is deionized double-distilled water. The chemical reactions were monitored by thin layer chromatography (TLC plate, purchased from Sigma) in the following experiments. The structure of compound was confirmed by nuclear magnetic resonance apparatus (400-MR DD2, manufactured by Agilent), the purity of compound was examined by high-performance liquid chromatography (Agilent 1200, Agilent), and the molecular weight of compound was measured by liquid chromatography-mass spectrometry (LC-MS, Agilent 6400, Agilent).

Example 1

In this example, the compounds of formulae a-f were synthesized, respectively.

Synthesis of the Compound of Formula a

Synthesis of Intermediate I

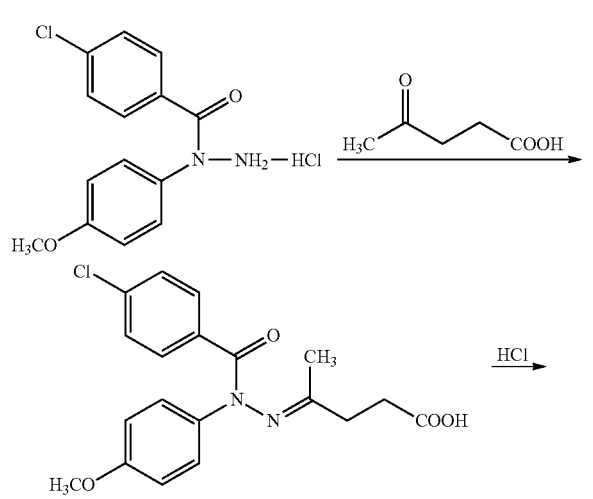

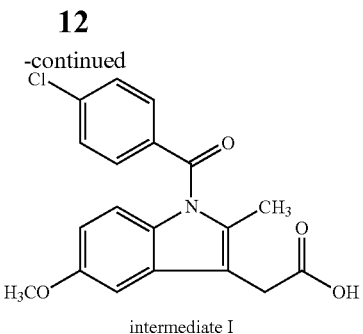

intermediate I (1) To a dry and clean reaction flask, 200 ml of ethanol, N-(p-chlorobenzoyl)-(p-methoxyphenyl)hydrazine (2.6 g, 0.01 mol), levulinic acid (2.3 g, 0.02 mol) and hydrochloric acid (0.37 g, 0.01 mol) were added under stirring, and refluxed under nitrogen for 5 hours. The reaction product was extracted with dichloromethane, washed with 2% NaOH and dried with anhydrous sodium sulfate to give a white solid with a yield of 51%. (2) The white solid (1.8 g, 0.005 mol) prepared in the above step was dissolved in 50 ml of dichloromethane, hydrochloric acid (0.37 g, 0.01 mol) was added dropwise, and the reaction was performed under reflux for 18 hours. The reaction product was washed with saturated sodium carbonate solution, extracted with dichloromethane, dried with anhydrous sodium sulfate and recrystallized from isopropanol to give a gray solid with a yield 87%.

$^1$H NMR (DMSO-d6) δ 8.24 (d, J=8.9 Hz, 1H), 7.82 (d, J=8.5 Hz, 2H), 7.73 (d, J=8.4 Hz, 2H), 7.39 (s, 1H), 7.19 (d, J=2.3 Hz, 1H), 7.06 (dd, J=2.4 Hz, 8.9 Hz, 1H), 3.87 (s, 3H), 3.73 (s, 2H).

Synthesis of Intermediate II

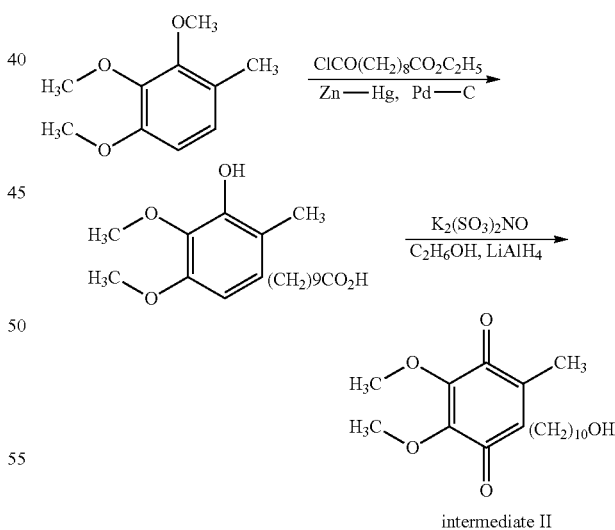

intermediate II (1) To a dry and clean reaction flask, dichloromethane (20 ml), 3,4,5-trimethoxytoluene (1.82 g, 0.01 mol), 10-acetoxydecanoyl chloride (2.73 g, 0.015 mol) were added under stirring, then anhydrous aluminum trichloride powder (3.33 g, 0.025 mol) was added, and the reaction was started after cooling to 4° C. in an ice-water bath. After 3 days, 0.5 ml of 10% palladium-carbon was added, and the reaction was continued at 25° C. for 8 hours. After the reaction was finished, 50 ml of ice water was poured into the reaction flask, and then 20 ml of dichloroethane was added for extraction. The extract was dried with anhydrous sodium sulfate to give 3.10 g of colorless oil with a yield of 83%. (2) The product (3 g, 0.01 mol) prepared in the above step was dissolved in 30 ml of DMF, added with 2 equivalents of Fremy's salt/($K_2[ON(SO_3)_2]$) and 0.1 equivalents of potassium dihydrogen phosphate, stirred at 50° C. for 8 hours, and then dropwise added with ethanol (0.12 g, 0.025 mol) and hydrochloric acid (0.37 g, 0.01 mol). The reaction was performed at 50° C. for 8 hours. The reaction product was extracted with dichloromethane, and used directly to perform the subsequent reaction: the product (1.6 g, 0.005 mol) extracted with dichloromethane was dissolved in 20 ml of DMF, added with lithium aluminum hydride (0.19 g, 0.005 mol), and allowed to react at 80° C. for 3 hours. The reaction mixture was extracted twice with dichloromethane, dried with anhydrous sodium sulfate, distilled under reduced pressure to dryness, and recrystallized from a mixed solvent of n-hexane and diethyl ether to give 2.2 g of orange needlelike product (intermediate II), with a yield of 63% and HPLC content of 98.10%. $^1$H NMR (400 MHz, CDCl$_3$, ppm): δ1.28[br, s, 14H], 1.53[br, s, 2H], 2.01 [s, 3H], 2.44[t, 2H], 3.64[t, 2H], 3.98[d, 6H].

In this example, the compound of formula a was synthesized according to the following scheme:

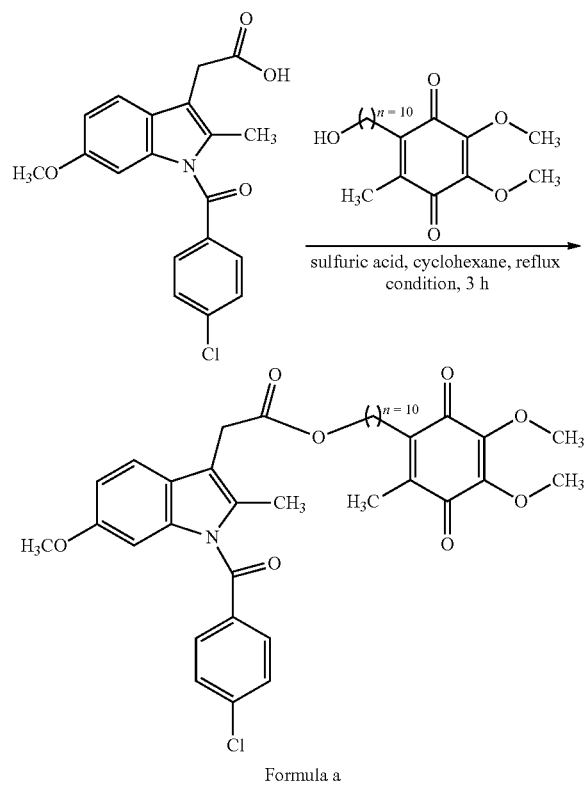

Formula a

Intermediate II (508 mg, 1.5 mmol) was dissolved in 10 ml of anhydrous cyclohexane, placed in a four-necked flask equipped with a stirrer, a condenser, an oil-water separator and a thermometer, heated (65° C.) and stirred until it was dissolved thoroughly. 21 mg (0.21 mmol) of concentrated sulfuric acid was added dropwise slowly under vigorous stirring. After the dropwise addition of sulfuric acid was finished, the mixed solution was heated to 25° C., and the intermediate I (1610 mg, 4.5 mmol) was added dropwise. After completion of the addition, the mixture was subjected to reflux and water separation for 3-8 hours. The reaction was monitored by TLC. After the signal of intermediate II could not be detected, the following treatment was carried out: the reaction system was cooled to room temperature, and added with a saturated aqueous solution of sodium carbonate for neutralization until the aqueous phase was neutral. The system was allowed to stand, and the organic layer and aqueous layer were separated. The organic phase was washed with water (25 ml×3), and centrifuged or filtered under reduced pressure. Then the filter cake of the centrifugal sediment was dissolved in 25 ml of cyclohexane, and mixed with 25 ml of mixed solution (12.5 ml of methanol+12.5 ml of saturated sodium carbonate solution), and the organic phase was further separated. The organic phase was washed with 25 ml of mixed solution (12.5 ml of methanol+12.5 ml of sodium carbonate solution), dried with anhydrous magnesium sulfate for 2 hours, and subjected to rotary evaporation under reduced pressure to give a red-brown jelly-like product (yield: 78%, purity: 98.3%). $^1$H NMR (400 MHz, CDCl$_3$, ppm): 7.68 (2H, dd, J=2 Hz, 6.5 Hz), 7.48 (2H, dd, J=2 Hz, 6.5 Hz), 6.98 (1H, d, J=2 Hz), 6.88 (1H, d, J=9 Hz), 6.68 (1H, dd, J=2 Hz, 9 Hz), 5.93 (t, 1H, J=11.0 Hz), 5.60 (m, 1H), 5.35-5.26 (m, 1H), 5.20-4.94 (2H, broad), 4.63 (2H, d, J=6.5 Hz), 3.99 (s, 6H, 2×-OCH$_3$), 3.41 (t, J=6.8 Hz, 2H, —CH$_2$—), 2.45 (t, J=7.7 Hz, 2H, ubquinone-CH$_2$—), 2.02, (s, 3H, —CH$_3$), 1.89 (J=7.4 Hz, 2H, —CH$_2$—CH$_2$—), 1.42-1.28 (m, 14H, —(CH$_2$)$_7$—. LC-MS:C$_{38}$H$_{44}$ClNO$_8$, M/Z(M-H) 678.23.

Synthesis of the Compound of Formula b

The compound of formula b was synthesized according to the following scheme:

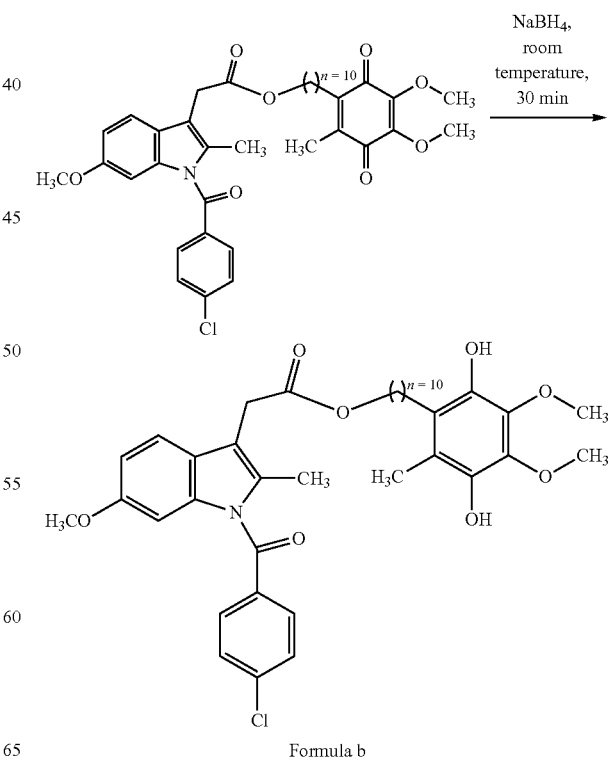

Formula b

The synthetic and purified compound a (1250 mg, 1.62 mmol) was dissolved in 15 ml of dichloromethane, and sodium borohydride/NaBH$_4$ (290 mg, 7.8 mmol) was slowly added under the protection of nitrogen. The reaction was performed under stirring at room temperature for 30 minutes. After completion of the reaction, excessive NaBH$_4$ was quenched with 2 ml of 5% hydrochloric acid. The reactor was charged with 50 ml of diethyl ether, and the organic phase was washed sequentially with 1.2 M hydrochloric acid (50 ml) and saturated aqueous solution of sodium chloride (2×50 ml). The organic phase was dried with magnesium sulfate, and solvent was evaporated under reduced pressure to give a yellowish brown jelly product (yield: 75%, purity: 97.1%), $^1$H NMR (400 MHz, CDCl$_3$, ppm): 7.69 (2H, dd, J=2 Hz, 6.5 Hz), 7.27 (2H, dd, J=2 Hz, 6.5 Hz), 6.86 (1H, d, J=2 Hz), 6.63 (1H, d, J=9 Hz), 6.51 (1H, dd, J=2 Hz, 9 Hz), 5.93 (t, 1H, J=11.0 Hz), 5.60 (m, 1H); 5.35-5.26 (m, 1H); 5.31 (s, 1H, —OH), 5.26 (s, 1H, —OH), 3.89 (s, 6H, 2×-OCH$_3$), 3.41 (t, J=6.8 Hz, 2H, —CH$_2$—Br), 2.59 (t, J=7.7 Hz, 2H, ubquinol-CH$_2$—), 2.15 (s, 3H, CH$_3$), 1.85 (quin, J=7.4 Hz, 2H, —CH$_2$—CH$_2$—), 1.44-1.21 (m, 14H, —(CH$_2$)$_7$—). LC-MS: C$_{38}$H$_{46}$ClNO$_8$, M/Z(M-H)680.23.

Synthesis of the Compound of Formula c

Synthesis of Intermediate III

Intermediate III was synthesized according to the procedure for the synthesis of the intermediate I of compound a, except that N-(p-chlorobenzoyl)-(p-methoxyphenyl)hydrazine and levulinic acid used in the synthesis of the intermediate I were replaced with ethyl 5-fluoro-2-methyl-3-indene acetate and p-methylthiophenaldehyde, and the product was recrystallized to give a pale yellow solid with a total yield of 59%. $^1$HNMR (400 MHz, CDCl$_3$) δ1.31 (d, J=6.9 Hz, 6H), 2.20 (s, 3H), 2.97 (s, J=6.9 Hz, 1H), 3.59 (s, 2H), 6.55-6.61 (m, 1H), 6.85-6.90 (m, 1H), 7.19 (s, 1H), 7.25-7.45 (m, 5H).

In this example, the compound of formula c was synthesized according to the following scheme:

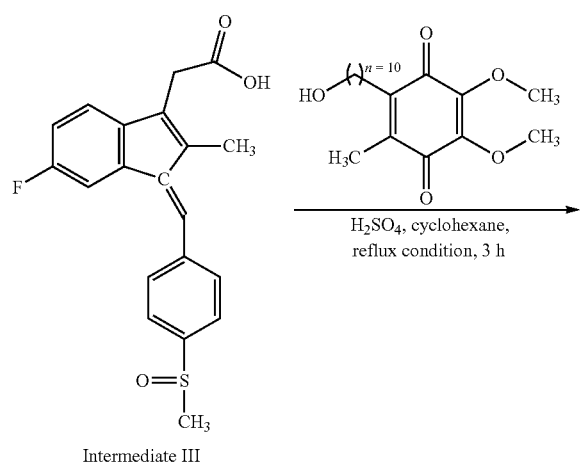

Intermediate III

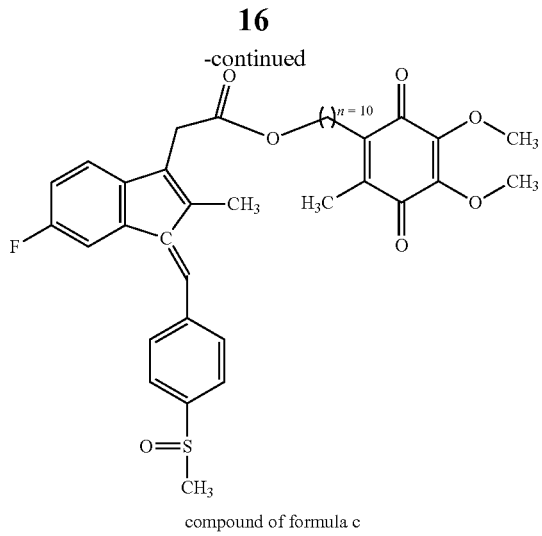

compound of formula c

Compound c was synthesized according to the procedure for the synthesis of compound a, except that the intermediate I for synthesizing compound a was replaced with intermediate III, and the reaction mixture was purified to give a reddish brown jelly-like product (yield: 81%, purity: 98.3%): $^1$H NMR (400 MHz, CDCl$_3$, ppm): 7.99 (d, J=7.8 Hz, 2H), 7.72 (d, J=7.8 Hz, 2H), 7.62 (dd, J=5.1 Hz, 7.8 Hz, 1H), 7.38 (s, 1H), 7.04-6.95 (m, 3H), 6.68 (1H, dd, J=2 Hz, 9 Hz), 5.93 (t, 1H, J=11.0 Hz); 5.60 (m, 1H); 5.35-5.26 (m, 1H); 5.20-4.94 (2H, broad), 4.63 (2H, d, J=6.5 Hz), 3.99 (s, 6H, 2×-OCH$_3$), 3.41 (t, J=6.8 Hz, 2H, —CH$_2$—), 2.45 (t, J=7.7 Hz, 2H, ubquinone-CH$_2$—), 2.02, (s, 3H, —CH$_3$), 1.89 (J=7.4 Hz, 2H, —CH$_2$—CH$_2$—), 1.42-1.28 (m, 14H, —(CH$_2$)$_7$—. LC-MS: C$_{39}$H$_{45}$FSO$_7$, M/Z(M-H)676.85.

Synthesis of the Compound of Formula d

In this example, the compound of formula d is synthesized according to the following scheme:

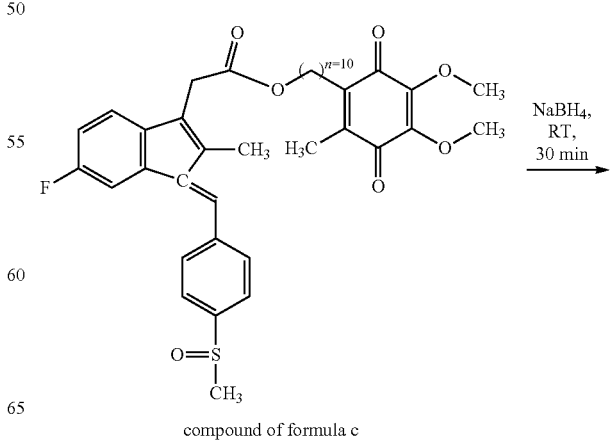

compound of formula c

17

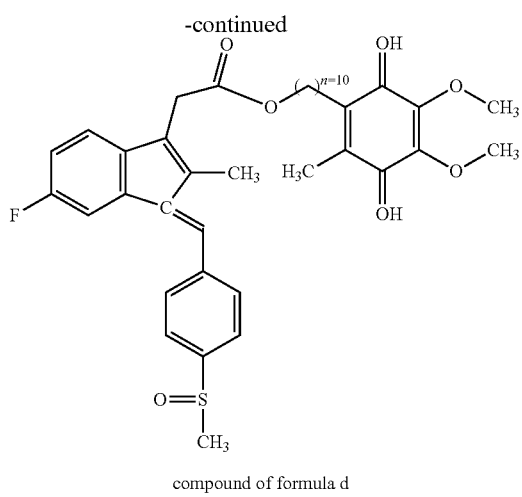

compound of formula d

The compound d was synthesized according to the procedure for synthesizing compound b above, except that compound a for the synthesis of compound b was replaced with compound c, and the reaction mixture was purified to give a yellowish brown jelly-like product (yield: 73%, purity: 97.2%), $^1$H NMR (400 MHz, CDCl$_3$, ppm): 7.61 (2H, dd, J=2 Hz, 6.5 Hz), 7.07 (2H, dd, J=2 Hz, 6.5 Hz), 6.86 (1H, d, J=2 Hz), 6.61 (1H, d, J=9 Hz), 6.51 (1H, dd, J=2 Hz, 9 Hz), 5.93 (t, 1H, J=11.0 Hz); 5.60 (m, 1H); 5.35-5.26 (m, 1H); 5.31 (s, 1H, —OH), 5.26 (s, 1H, —OH), 3.87 (s, 6H, 2×-OCH$_3$), 3.41 (t, J=6.8 Hz, 2H, —CH$_2$—Br), 2.72 (t, J=7.7 Hz, 2H, ubquinol-CH$_2$—), 2.25 (s, 3H, CH$_3$), 1.87 (quin, J=7.4 Hz, 2H, —CH$_2$—CH$_2$—), 1.39-1.23 (m, 14H, —(CH$_2$)$_7$—). LC-MS: C$_{39}$H$_{47}$FSO$_7$, M/Z(M-H)678.85.

Synthesis of Intermediate IV

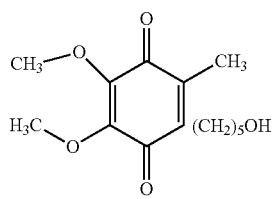

intermediate IV

The intermediate IV was synthesized according to the procedure described above for the synthesis of intermediate II except that 10-acetoxydecanoyl chloride used in the synthesis of intermediate II was replaced with 5-acetoxyvaleryl chloride, and the reaction mixture was purified to give a red oily liquid (total yield: 57%, purity: 98.2%). $^1$H NMR (CDCl$_3$) δ4.051 (t, 2H, J=6.87 Hz); 3.99 (s, 3H); 3.99 (s, 3H); 2.45 (t, 2H, J=7.15 Hz); 2.29 (t, 2H, J=7.42 Hz); 2.01 (s, 3H); 1.61-1.57 (m, 5H); 1.33-1.28 (m, 30H); 0.88 (t, 3H, J=6.60 Hz).

Synthesis of Intermediate V

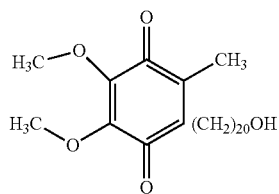

intermediate V

18

The intermediate V was synthesized according to the procedure described above for the synthesis of intermediate II except that 10-acetoxy decanoyl chloride used in the synthesis of intermediate II was replaced with 20-acetoxyeicosanoyl chloride and purified to give a pale red solid (total yield: 39%, purity: 97.3%). $^1$H NMR (CDCl$_3$) δ 5.41-5.30 (m, 4H); 4.05 (t, 2H, J=6.87 Hz); 3.98 (s, 6H); 2.77 (t, 2H, J=5.77 Hz); 2.45 (m, 2H); 2.29 (t, 2H, J=7.42 Hz); 2.08-2.01 (m, 3H); 2.01 (s, 3H); 1.64-1.57 (m, 3H); 1.39-1.29 (m, 30H); 0.88 (t, 3H, J=6.60 Hz).

Synthesis of the Compound of Formula e

Formula e

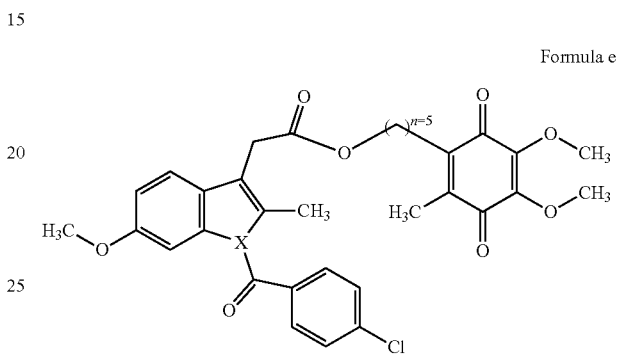

The compound e was synthesized according to the procedure described above for synthesizing compound a, except that the intermediate II used for the synthesis of the compound a was replaced with the intermediate IV, and the reaction mixture was purified to give reddish brown peptone-like product (total yield: 87%, purity: 98.2%) $^1$H NMR (400 MHz, CDCl$_3$, ppm): 7.73 (2H, dd, J=2 Hz, 6.5 Hz), 7.51 (2H, dd, J=2 Hz, 6.5 Hz), 6.92 (1H, d, J=2 Hz), 6.82 (1H, d, J=9 Hz), 6.65 (1H, dd, J=2 Hz, 9 Hz), 5.93 (t, 1H, J=11.0 Hz); 5.61 (m, 1H); 5.21-4.96 (2H, broad), 4.63 (2H, d, J=6.5 Hz), 3.99 (s, 6H, 2×-OCH$_3$), 2.45 (t, J=7.7 Hz, 2H, ubquinone-CH$_2$—), 1.99 (s, 3H, —CH$_3$), 1.73 (J=7.4 Hz, 2H, —CH$_2$—CH$_2$—), 1.43-1.25 (m, 6H, —(CH$_2$)$_3$—).

Synthesis of the Compound of Formula f

Formula f

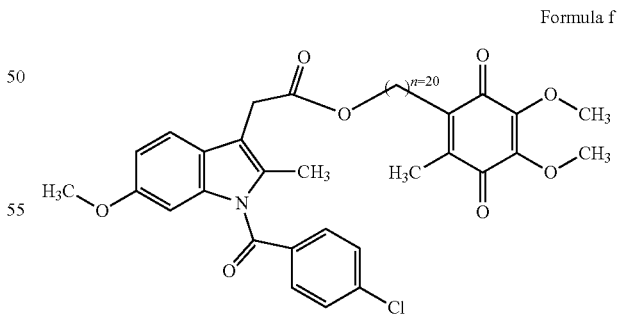

The compound of formula f was synthesized according to the procedure described above for synthesizing compound a, except that the intermediate II used for synthesizing compound a was replaced with the intermediate V, and the reaction mixture was purified to give a reddish brown, dry and thick matter (total yield: 69%, purity: 97.1%). $^1$H NMR (400 MHz, CDCl$_3$, ppm): 7.72 (2H, dd, J=2 Hz, 6.5 Hz), 7.51 (2H, dd, J=2 Hz, 6.5 Hz), 6.70 (1H, d, J=2 Hz), 6.89 (1H, d, J=9 Hz), 6.71 (1H, dd, J=2 Hz, 9 Hz), 5.97 (t, 1H, J=11.0 Hz); 5.66 (m, 1H); 5.38-5.29 (m, 1H); 5.22-4.97 (2H, broad), 4.63 (2H, d, J=6.5 Hz), 3.40 (s, 6H, 2×-OCH$_3$), 3.43 (t, J=6.8 Hz, 2H, —CH$_2$—), 2.47 (t, J=7.7 Hz, 2H, ubquinone-CH$_2$—), 2.05 (s, 3H, —CH$_3$), 1.91 (J=7.4 Hz, 2H, —CH$_2$—CH$_2$—), 1.43-1.31 (m, 34H, —(CH$_2$)$_{17}$—).

In the following examples, the compounds a-f prepared in Example 1 were used as sensitizer and protective agent to perform biological experiments and various analyses on biological activities and functions. In addition, comparative experiments were carried out using the protecting agents (amifostine) known in the art, the intermediate I and intermediate II prepared in the Example 1 above and other selective COX2 inhibitors. amifostine, paclitaxel, cisplatin, doxorubicin, 5-fluorouracil, celecoxib, EIA kits, terminal labeling kits and the like. All related reagents, which are used in the following examples, are purchased from Sigma-Aldrich and EMD Chemicals Inc. Cobalt 60 radiotherapy machine is Theratron from Atomic Energy Agency in Canada, and G50 biological gamma-ray irradiator is purchased from HOPEWELL in USA. SW480 cells (accession number CCL-228) are purchased from the American Standard Raw Materials Collection Center, and the mouse colon cancer cells MCA-38 are provided by the National Cancer Institute (Accession No. BNN-4050), both of which belong to the commercial products conventionally used in the art and can be obtained from many sources.

Statistical analysis of data: SPSS 12.0 software is used for statistical analysis, and the results of the data are expressed by x±s. In survival experiments, comparison of two samples adopts independent samples-T test. In other experiments, comparison of plural sample averages adopts one-way ANOVA, and comparison of the peripheral blood cell data adopts repeated measures ANOVA. P<0.05 means the difference has statistically significance.

Example 2

The Effect of the Compounds a-f of the Present Invention on the In Vivo Activity of COX1 and COX2

(1) COX-1 activity assay: 2 hours after intraperitoneal injection of calcium ionophore A23187 (50 mg/kg) to rats, each of the compounds a, b, c, d, e and f was orally administered (gavage) to three rats at a dose of 1, 3 and 9 mg/kg/day, respectively; the intermediate I was orally administered as a control drug to three rats at a dose of 0.5 mg/kg; and additional three rats were only administered with COX-1 activator, the calcium ionophore A23187, and were not administered with the compounds of the present invention. 6 hours after the compound of the present invention was administered, the animals were sacrificed, gastric mucosal tissue and myocardial tissue were collected, homogenized, and subjected to high-speed centrifugation (12,000 rpm), and the supernatant was collected for use. The amount of thromboxane B2 was measured using an enzyme-linked immunosorbent assay (EIA) kit (operated in accordance with the instructions provided by the manufacturer) and converted to COX1 activity.

(2) COX-2 activity assay: The assay was similar to that of COX-1, except that LPS was injected intraperitoneally to rats at a dose of 2.5 mg/kg to activate COX-2 in this experiment. After administration, the content of PGE2 in gastric mucosa was measured using an enzyme-linked immunosorbent assay (EIA) kit (operated according to the instructions provided by the manufacturer) and converted to COX2 activity.

Figure 1B:
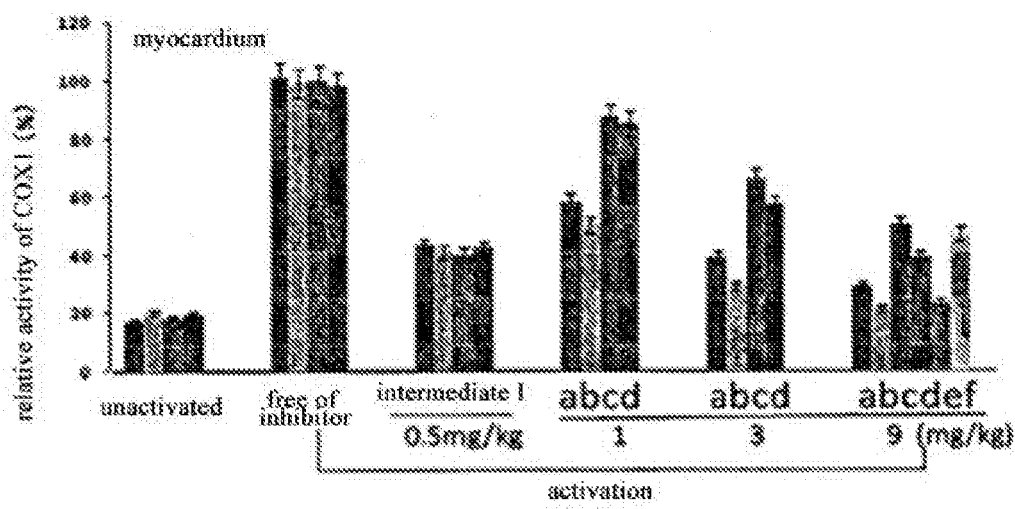
FIG. 1b shows the inhibitory effect of the compounds of the present invention on COX1 activity in myocardium.
Figure 1C:
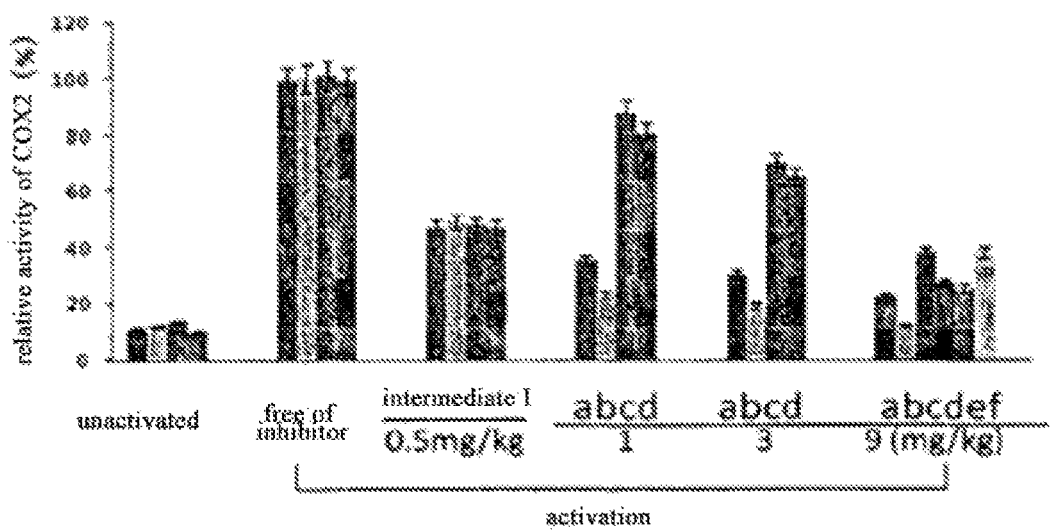
FIG. 1c shows the inhibitory effect of the compounds of the present invention on COX2 activity.

The percentage inhibition rate against COX-1 (FIG. 1a—gastric mucosa, FIG. 1b—myocardium) and COX-2 (FIG. 1c) and the IC$_{50}$ values (Table 1a—gastric mucosa; Table 1b—myocardium) of each tested pharmaceutical compound were calculated from the above data. The above data indicate that the inhibition against COX-1 in gastric mucosal tissue caused by the compounds a, b, c, d, e and f was reduced by nearly 700-fold compared with that of the intermediate I, and they almost lose the effect of inhibiting COX-1 in gastric mucosa. It can be seen that the gastrointestinal toxicity of compounds a, b, c, d, e and f has been significantly reduced. On the other hand, the compounds of the present invention have an enhanced inhibitory effect on COX-1 in myocardium, which is basically equivalent to the inhibitory effect of the intermediate I. The reason why the inhibition against COX-2 caused by compounds a and b is significantly enhanced may be the higher bioavailability of compounds a and b compared with the intermediate I, and another reason is that the compounds a and b of the present invention comprise the structures of intermediates I and II simultaneously, and the antioxidant function exhibited in the meantime can effectively inhibit endotoxin from activating COX-2. It can be seen from the data shown in FIGS. 1a and 1b that, since the compound of the present invention comprises the structures of intermediate I and II simultaneously, the combination of these two structures exhibits a significant synergistic effect on the inhibition against COX-2. The inhibitory effects of compounds c, d, e and f on COX-2 were weaker than those of compounds a and b.

Example 3

Figure 2:
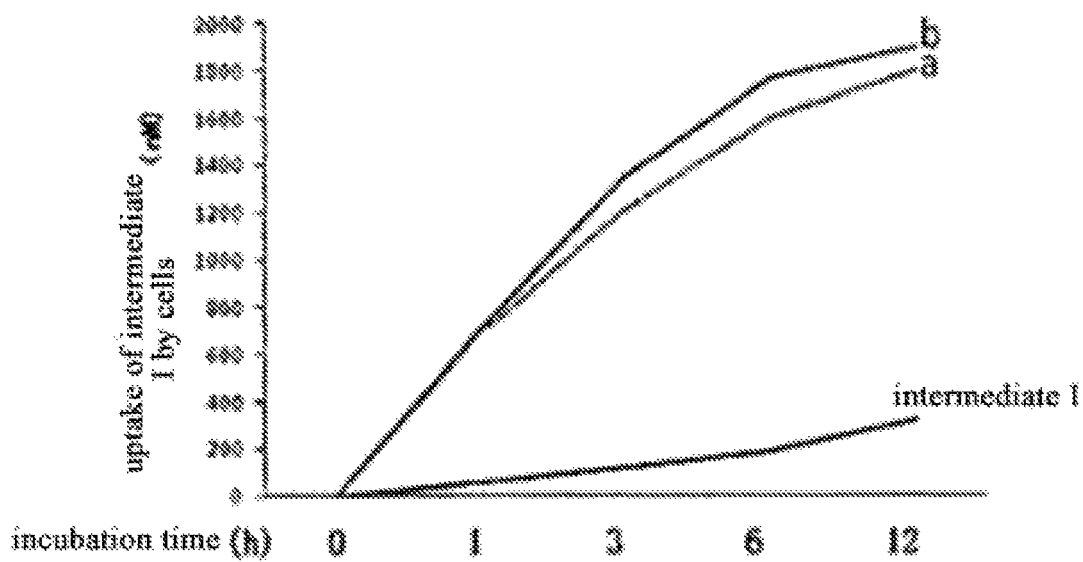
FIG. 2 shows the efficiency of the compounds of the present invention entering cells.

Measurement of cellular uptake of compounds: SW480 cells were inoculated in a 24-well culture dish and cultured in monolayer. When the culture reached a confluence of 80%, compounds a and b (each 10 μM) and intermediate I (10 μM) were added to the culture dish, and the cells were further incubated at 37° C. for 1, 3, 6, and 12 hours, respectively. The cells were washed fully with PBS (phosphate buffer solution) at various time points, and the cells were collected, extracted with acetonitrile, and centrifuged at a high speed (12,000 rpm) for 5 minutes. The amount of intermediate I dissolved in acetonitrile was measured by HPLC, and converted into the level of cellular uptake of intermediate I. During HPLC detection, a Thermo Hypersil BDS C18 column (150×4.6 mm, particle size of the packing is 3 μm) was used, the mobile phase was the solution of formic acid: CH$_3$CN:H$_2$O=0.3:4.7:95 (v/v/v), and the flow rate is 1 ml/min. The results are shown in FIG. 2, indicating that the ability of compounds a and b to enter cells is at least 6 times higher than that of the intermediate I. This indicates that the intermediate I is difficult to be efficiently taken up by the cells, and the compounds a and b have excellent properties of uptake by cells.

Example 4

Figure 3:
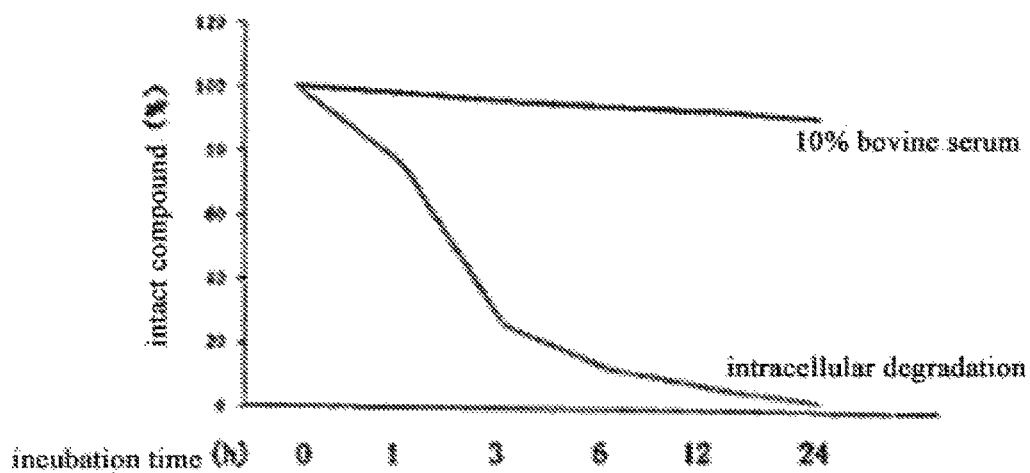
FIG. 3 shows the stability of the compound a of the present invention in plasma environment and in cells.

Determination of the stability of the compound: (1) degradation of the compound in plasma: Compound a (10 μM) dissolved in DMSO was cultured with 10% bovine serum medium (5 mL) at 37° C. 200 μL of medium was collected at the time points of 1, 3, 6, 12 and 24 hours, respectively, added with equal volume of acetonitrile for reaction, and subjected to high speed centrifugation (13,000 rpm) for 5 minutes. The level of degradation of the compound was determined by HPLC. The results are shown in FIG. 3. (2) Degradation of the compound in cells: the compound a dissolved in DMSO was added at a final concentration of 10 μM to a 6-well culture dish containing SW480 cells and incubated in carbon dioxide incubator. The cells were collected at the time points of 1, 3, 6, 12, and 24 hours, respectively, washed fully, then extracted with 0.5 mL of acetonitrile, and centrifuged at high speed (12,000 rpm) for 5 minutes. The level of degradation of the compound in the organic phase was determined by HPLC. The results are shown in FIG. 3. It can be seen that the compound a is quite stable in bovine serum, and only 11% of the compound a is hydrolyzed within 24 hours; the hydrolysis velocity significantly increases in cells, wherein almost 80% of the compound a is hydrolyzed within 3 hours, and the compound a is completely hydrolyzed within 24 hours.

Example 5

Figure 4A:
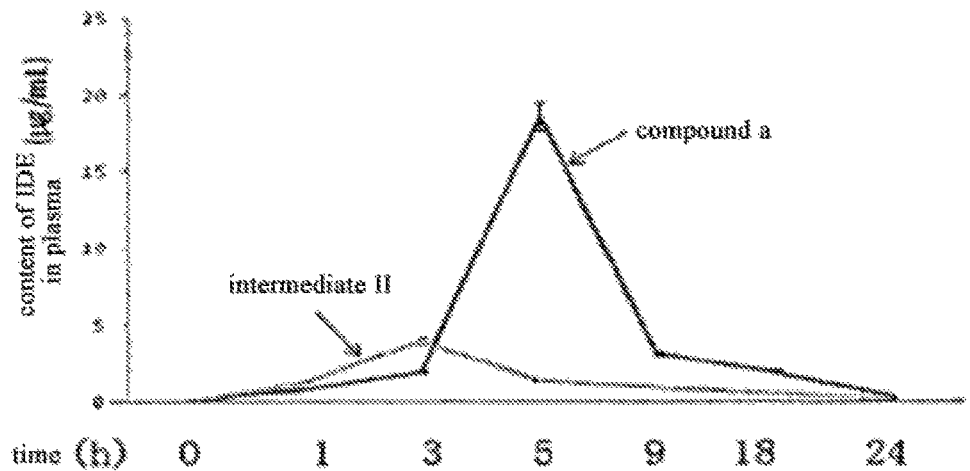
FIG. 4a shows the metabolic kinetics of the compounds of the present invention in animal bodies.
Figure 4B:
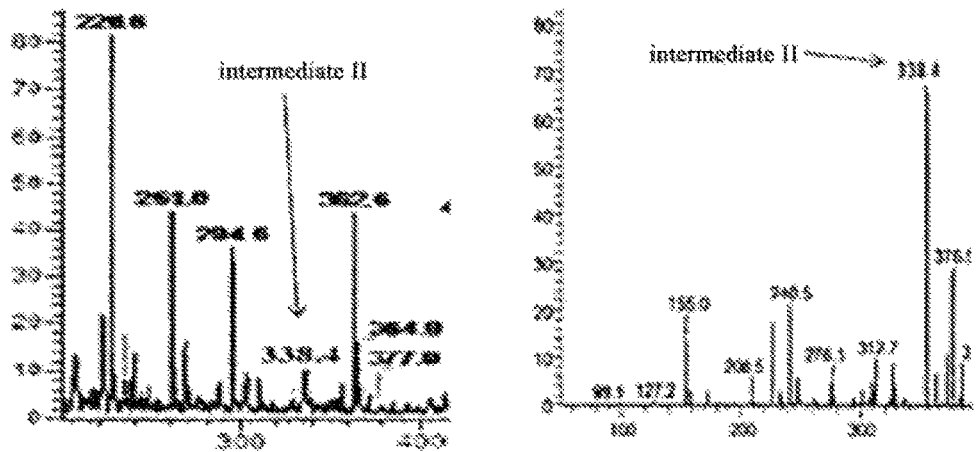
FIG. 4b shows the content of intact intermediate II in plasma after the compounds of the present invention is orally administered by animals.

Metabolic kinetics of the compound a in mice: the compound a and the intermediate II were administered to mice respectively by gavage at a dose of 25 mg/kg each time and 12 mg/kg each time (equimolar concentration). Equal volume of blood samples were collected at the time points of 1, 3, 5, 9, 18 and 24 hours, and centrifuged immediately. 100 μL of supernatant (plasma) was got, added with 2-fold volume of acetonitrile immediately to extract the blood samples twice, and centrifuged at high speed (12,000 rpm) for 5 minutes. The level of the intermediate II in the organic phase was determined by HPLC, and the content of the compound fragments was detected by LC-MS. Pharmacokinetics was analyzed by Pharmacokinetics Solutions 2.0 software (Summit Research Services, Montrose, Colo., USA). The results are shown in FIG. 4a and Table 1. The results show that the content of the intermediate II in the plasma of mice orally administered the compound a was significantly higher than that in the plasma of mice orally administered intermediate II, and the metabolites in the plasma of mice orally administered the compound a were significantly reduced (see FIG. 4b), indicating that the compound a avoids the first pass effect to a large extent and effectively improves the bioavailability of drugs.

TABLE 1

Pharmacokinetics of compounds

|  | $T_{max}$ (h) | $C_{max}$ (μg/mL) | $AUC_0$ (μg · hr/mL) | $T_{1/2}$ (h) |
|---|---|---|---|---|
| intermediate II | 2.50 | 3.7 | 10.2 | 3.8 |
| compound a | 5 | 19.8 | 63.2 | 7.6 |

Example 6

Figure 5:
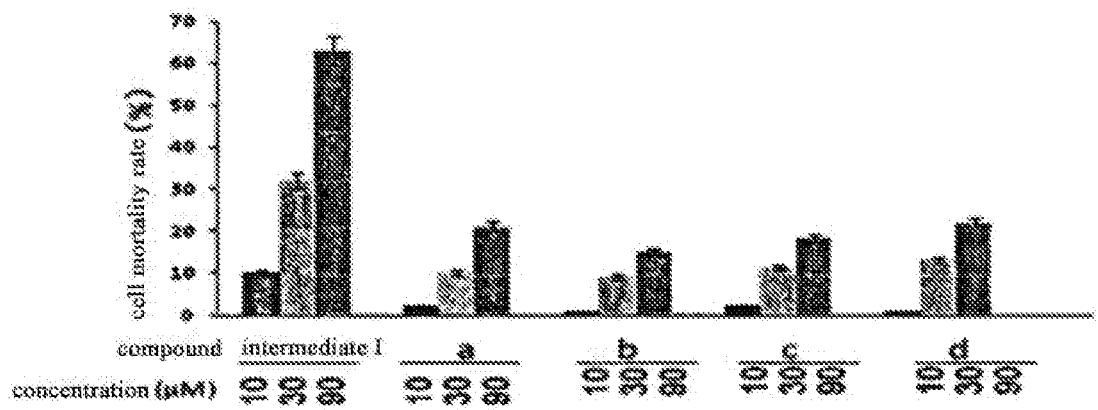
FIG. 5 shows the toxicity of the compounds of the present invention to normal cells.

Analysis on toxicity of the compounds a, b, c and d: (1) intestinal mucosa cells (intestinal mucosa cells made by traditional trypsin digestion method in laboratory) primarily cultured in 96-well plate were treated with various concentrations (10, 30 and 90 μM) of the compounds a, b, c and d, as well as the corresponding concentrations of intermediate I and comparative compound A. 24 hours later, the degree of damage of the cells was detected by lactate dehydrogenase release (LDH) (operating according to the operating instructions provided by the manufacturer). The results are shown in FIG. 5. It can be seen that when the concentration of intermediate I reaches 30 μM, evident cell death occurs; and when the concentration of compounds a, b, c or d reaches 90 μM, there is still no evident cell death, which indicates that the toxicities of compounds a, b, c, d to normal cells are significantly lower than that of the intermediate I. The low toxicity of the compounds of the present invention may be due to the function of resisting oxidative damage caused by the structure of intermediate II in the compounds.

(2) Various concentrations (10, 30 and 90 μM) of the compounds a and b and corresponding concentrations of the intermediate I were orally administered to rats (each experiment was repeated on six rats) by continuous gavage for three times. 12 hours after the last gavage, the rats were sacrificed, and the stomach was taken out by operation, dissected along the greater curvature, washed with physiological saline, and fixed with formalin for 15 minutes. Then a binocular magnifying glass was used to observe the lesions of the gastric mucosa. 5 lesions were counted for each rat. The ulcer indexes of the animals using the largest dose (90 μM) of IND and compounds were calculated: ulcer index= (L1+W1+L2+W2+L3+W3+L4+W4+L5+W5+L6+W6)/6, wherein L represents the length of the ulcer, W represents the width of the ulcer, the longest and widest lesions (mm) were recorded. The results are shown in Table 2a. It can be seen that only one rat has light ulcer in the group administered the compound a at a high concentration, the compound b, even at a high concentration, does not result in ulcer, while each animal in the group administered the intermediate I at the same concentration has very serious ulcer (see Table 2b). The compound a of the present invention is a compound formed by esterification of the intermediates I and II, and its toxicity is lower than that of the intermediate I in acid form. There is no esterified product of the intermediate I that has been found to have such a low side effect of inducing ulcer in the art. This unexpected technical feature of the product of the present invention cannot be explained only by the fact that esterification causes loss of the activity of inhibiting COX1. At this point, the inventor believes that compounds a and b of the present invention contain the structures derived from intermediates I and II at the same time, and the intermediate II brings about significant antioxidant effect which combines with the effect of esterification to form synergy and achieve the above-mentioned excellent effect of reducing gastrointestinal injury.

TABLE 2a

Comparative experiments of the side effect of inducing ulcer between the intermediate I and the compounds of the present invention.

| Compounds | Dose (μM/kg) | Ulcer index |
|---|---|---|
| Solvent (DMSO) control | 90 | 0 |
| Intermediate I | 90 | 72.8 ± 6.82 |
| Compound a | 90 | 3.3 ± 0.12* |
| Compound b | 90 | 0 |

TABLE 2b

Comparative experiments of the prevalence of ulcer between the intermediate I and the compounds of the present invention

| intermediate I(μM) | prevalence of ulcer | a (μM) | prevalence of ulcer | b (μM) | prevalence of ulcer |
|---|---|---|---|---|---|
| 10 | 0/6 | 10 | 0/6 | 10 | 0/6 |
| 30 | 2/6 | 30 | 0/6 | 30 | 0/6 |
| 90 | 6/6 | 90 | 1/6 | 90 | 0/6 |

Example 7

Figure 6A:
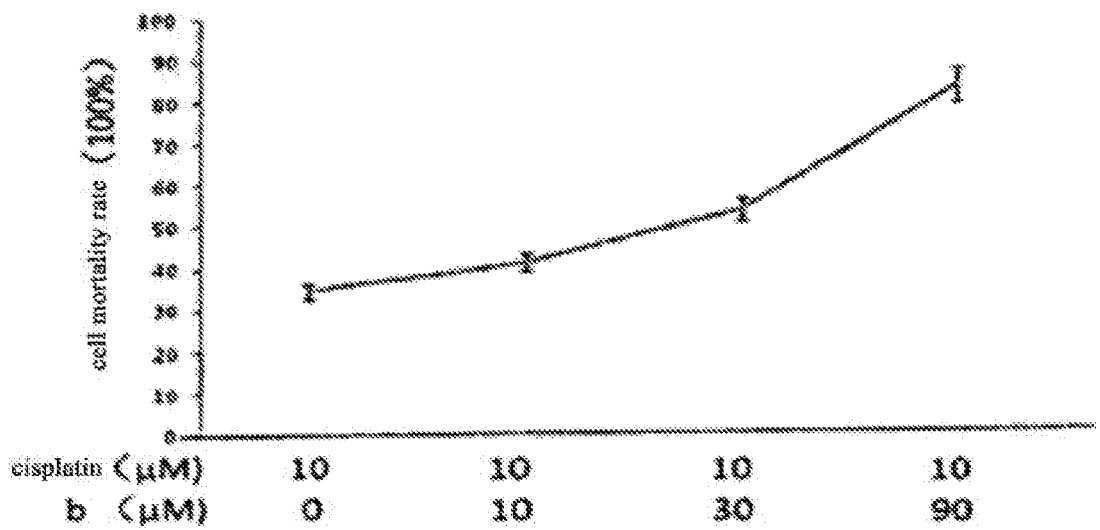
FIG. 6a shows that the compounds of the present invention selectively enhance the killing effect of cisplatin on tumor cells.
Figure 6B:
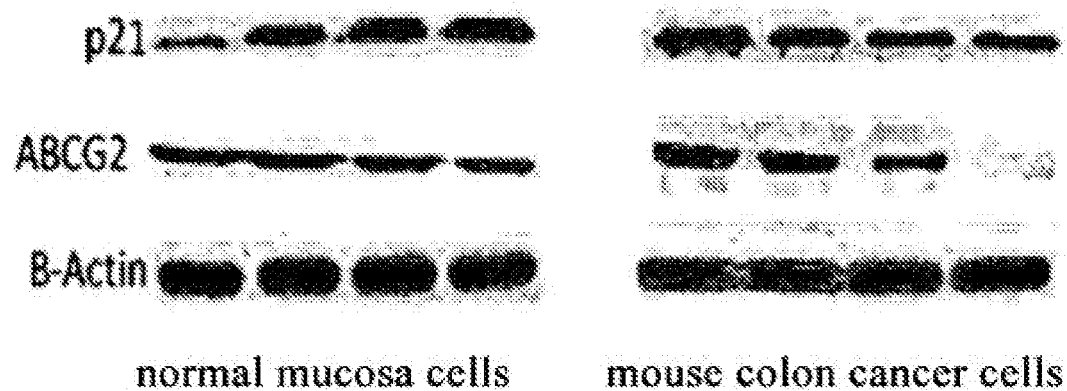
FIG. 6b shows the influence of the compounds of the present invention on the expression of normal cells and the tumor cells ABCG2 and P21.

The mechanism of compounds enhancing killing effect of chemotherapeutic agents on tumor cells while protecting normal cells: mouse colon cancer cells (MCA-38) and primarily-cultured normal mouse intestinal mucosa cells were cultured in a 96-well plate, respectively. 24 hours later, various concentrations (10, 30 and 90 μM) of compound b was respectively added to the cell culture medium, and incubated for 24 hours. LDH was used to detect the damage of the cells, and the cells were collected and extracted for protein. The expression levels of adenosine triphosphate-binding transporter (ABCG2) and the cell cycle-dependent protein kinase (p21) were detected by immunoblotting (performed according to the instructions provided by the manufacturer). The results are shown in FIGS. 6a and 6b. The compound b at all tested concentrations significantly enhances the killing effect of cisplatin on clone cancer cells. Surprisingly, all tested concentrations except the high concentration of the compound b significantly inhibit cisplatin from damaging normal intestinal mucosa cells (FIG. 6a); compound b can significantly inhibit expression of adenosine triphosphate-binding transporter (ABCG2) in tumor cells (FIG. 6b), but has no influence on the expression of ABCG2 in normal cells. ABCG2 is a transporter, and can pump anticancer drugs out of the cells. Hence, the compound b can accumulate anti-cancer drugs in tumor cells at a high concentration, thereby enhancing the killing effect of chemotherapeutic drugs on tumor. In addition, the compound b can significantly enhance the expression of p21 in normal intestinal mucosa cells, but has no influence on the expression of p21 in tumor cells. The high expression of p21 allows the cells to be in non-dividing quiescent phase, so that cells are not sensitive to chemotherapeutic drugs or injury in other forms. The compounds of the present invention make these proteins expressed differentially in normal tissues and tumor tissues, which is one of the reasons for selectively protecting normal tissues and enhancing the sensitivity of tumors to treatment.

Example 8

Figure 7:
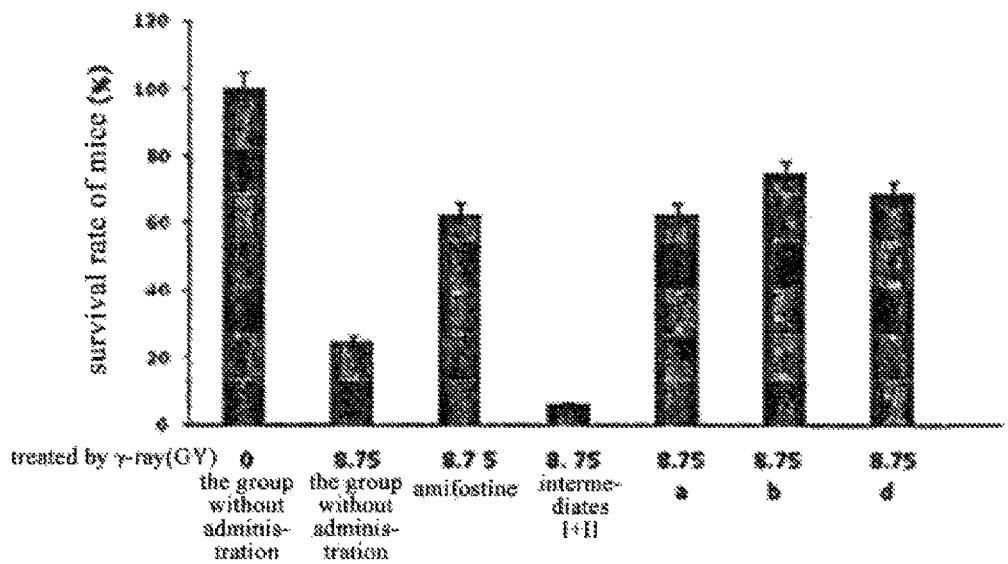
FIG. 7 shows the influence of the compounds of the present invention on survival rate of mice induced with gamma ray.

Effect of compound b as a protective agent on the survival rate of mice irradiated by γ-rays In this experiment, 10-week-old male mice (C57BL/6J) weighing about 20 g were used as subjects, and 16 mice were taken as a group. The mice were divided into the following groups: 1. no γ-ray+no drug; 2. γ-ray+no drug; 3. γ-ray+amifostine; 4. γ-ray+intermediate I+intermediate II; 5. γ-ray+compound a; 6. γ-ray+compound b; and 7. γ-ray+compound d. Firstly, each group of mice was administered with a protective agent, and the specific amounts were as follows: compound a, b and d: 6 mg/kg/day (8.1 μM), amifostine: 400 mg/kg/day (1.5 mM), intermediate I+Intermediate II: each 3 mg/kg/day (8.1 μM). Except that amifostine was intraperitoneally injected (30 minutes before irradiation, amifostine was administered), the other protective agents were administered by gavage. 12 hours after administration, systemic irradiation was performed using cobalt 60γ-rays at a dose of 8.75Gy and a dose rate of 0.35 Gy/min for 25 minutes, with the radiation source 80 cm away from the mice. The mice were irradiated once, and continuously administered with drugs once daily for 10 days after irradiation. The number of survival mice was recorded. The percentage obtained by dividing the number of survival mice by the total number of mice in the experimental group (16 mice) is survival rate of mice, and the results are summarized in FIG. 7. In the control group receiving no protective agent and being irradiated at a dose of 8.75 Gy, 4 mice are survived at the 30$^{th}$ day, and the survival rate is 25%; in the group receiving the compound a, 10 mice are survived at the 30$^{th}$ day, and the survival rate is 62.5%; in the group receiving the compound b, 12 mice are survived at the 30$^{th}$ day, and the survival rate is 75%; in the group receiving amifostine, 10 mice are survived at the 30$^{th}$ day, and the survival rate is 62.5%; and in the group receiving the compound d, 11 mice are survived at the 30$^{th}$ day, and the survival rate is 68.75%. It is noteworthy that in the experimental group using intermediate I+intermediate II, only one mouse is survived. It can be seen from the above experimental data that compound b can significantly reduce the death of animals induced by ray, especially the protective effect of compound b is better than amifostine.

Example 9

The protective effects of compounds a and b on blood cell damage induced by paclitaxel.

Figure 8:
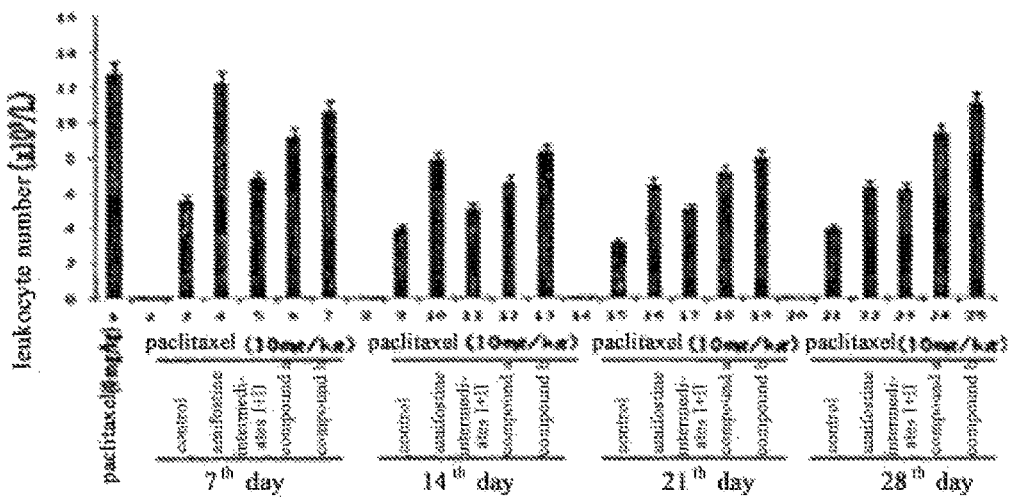
FIG. 8 shows the protective effect of the compounds of the present invention on paclitaxel-induced peripheral leukocyte injury in animals.

In this experiment, 10-week-old male mice (C57BL/6J) weighing about 20 grams were used as subjects, and 6 mice were taken as a group. The mice were divided into 5 groups: 1. Paclitaxel; 2. Paclitaxel+amifostine; 3. Paclitaxel+intermediate I+intermediate II; 4. paclitaxel+compound a; and 5. paclitaxel+compound b. Firstly, each group of mice was administered with a protective agent, and the specific amounts were as follows: compounds a and b: each 6 mg/kg/day (8.1 μM), amifostine: 400 mg/kg/day (1.5 mM), intermediate I+Intermediate II: each 3 mg/kg/day (8.1 μM). Except that amifostine was intraperitoneally injected (30 minutes before administering Paclitaxel, amifostine was administered), the other protective agents were administered by gavage (once a day, 25 times continuously). 12 hours after the compound a and the corresponding protective agents were administered, Paclitaxel was intraperitoneally injected (10 mg/kg/day, once every 3 days, 9 times continuously), and 7, 14, 21, 28 days later, blood of mice was drawn respectively. The number of leukocytes was analyzed. The results are shown in FIG. 8. From the experimental results, it can be seen that compared with amifostine known in the prior art and intermediate I, using compounds a and b can apparently reduce radiation-induced peripheral leukocyte damage and significantly increases the number of peripheral blood cells under simulated chemotherapy conditions. It is notable that the protective effect of amifostine on leukocyte is slight better than that of the compounds a and b at the early stage of simulated chemotherapy, but the protective effect of compounds a and b on leukocytes is significantly better than that of amifostine at the late stage of chemotherapy. Compound b provides the strongest protective effect.

Example 10

In vivo inhibitory effect of the compounds of the present invention on the transplanted tumors in nude mice induced by chemotherapeutic agent and selective effects of the compounds of the present invention on the normal tissues (in vivo experiments).

Figure 9A:
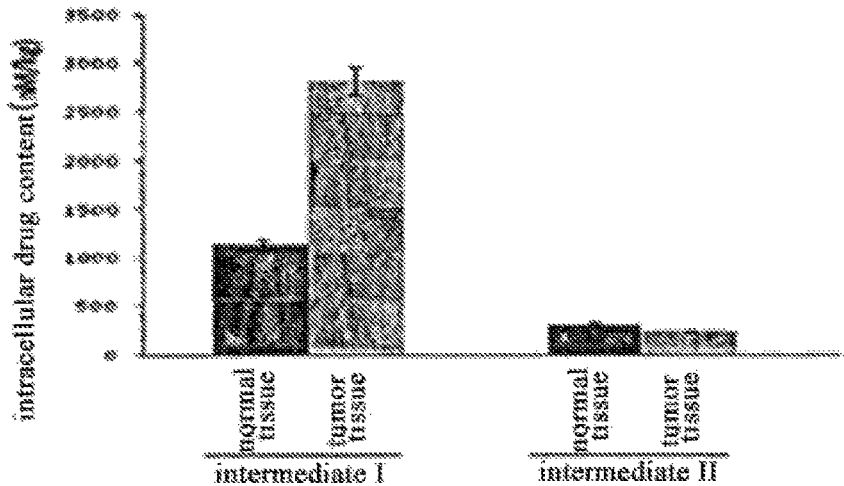
FIG. 9a shows the content of the active ingredients (intermediate I, intermediate II), generated by hydrolysis of the compound of the present invention, in tumor tissue and normal peripheral tissue.
Figure 9B:
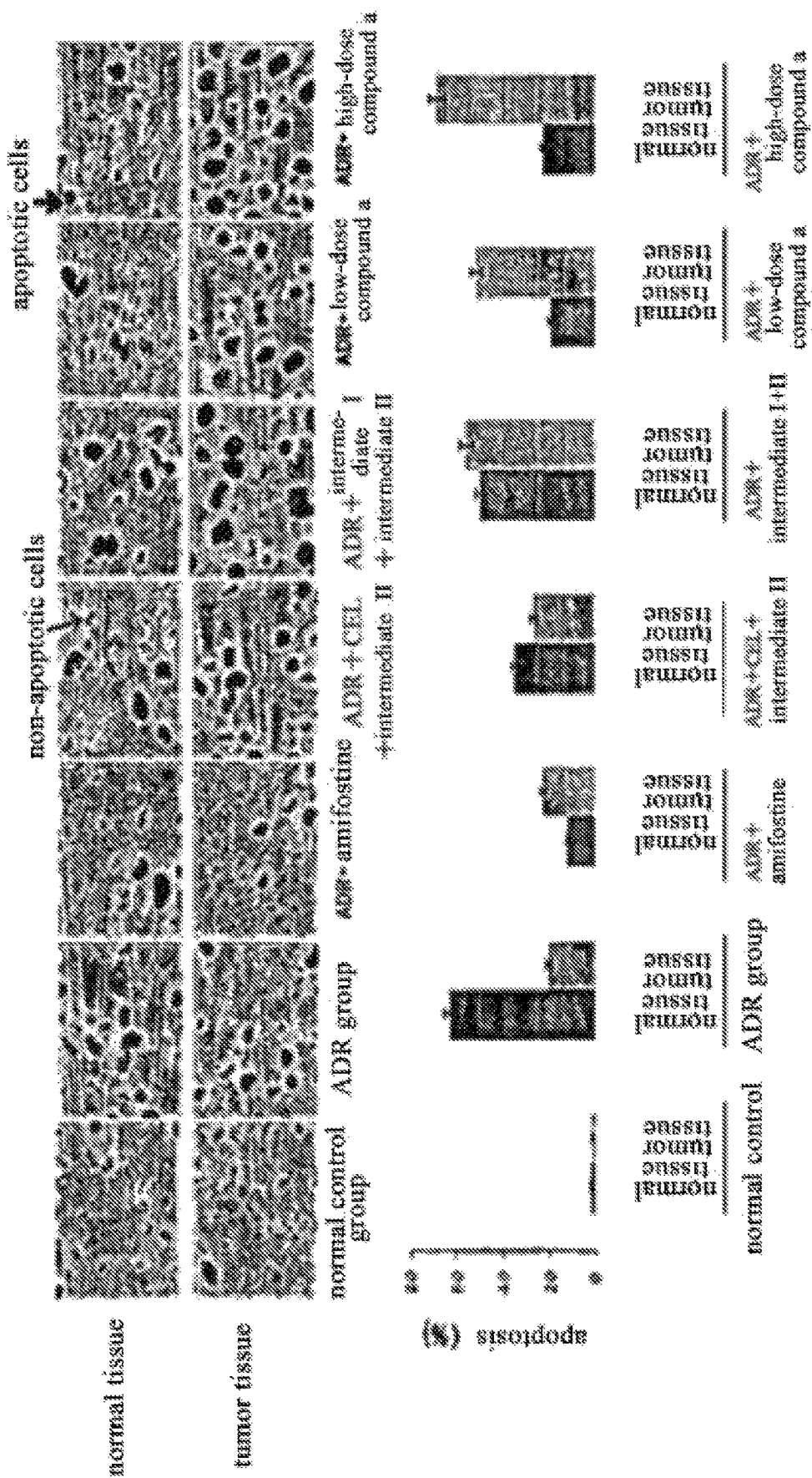
FIG. 9b shows that the compounds of the present invention protect normal tissues from the killing of chemotherapeutic agents while enhancing the killing of chemotherapeutic agents on tumor.
Figure 9C:
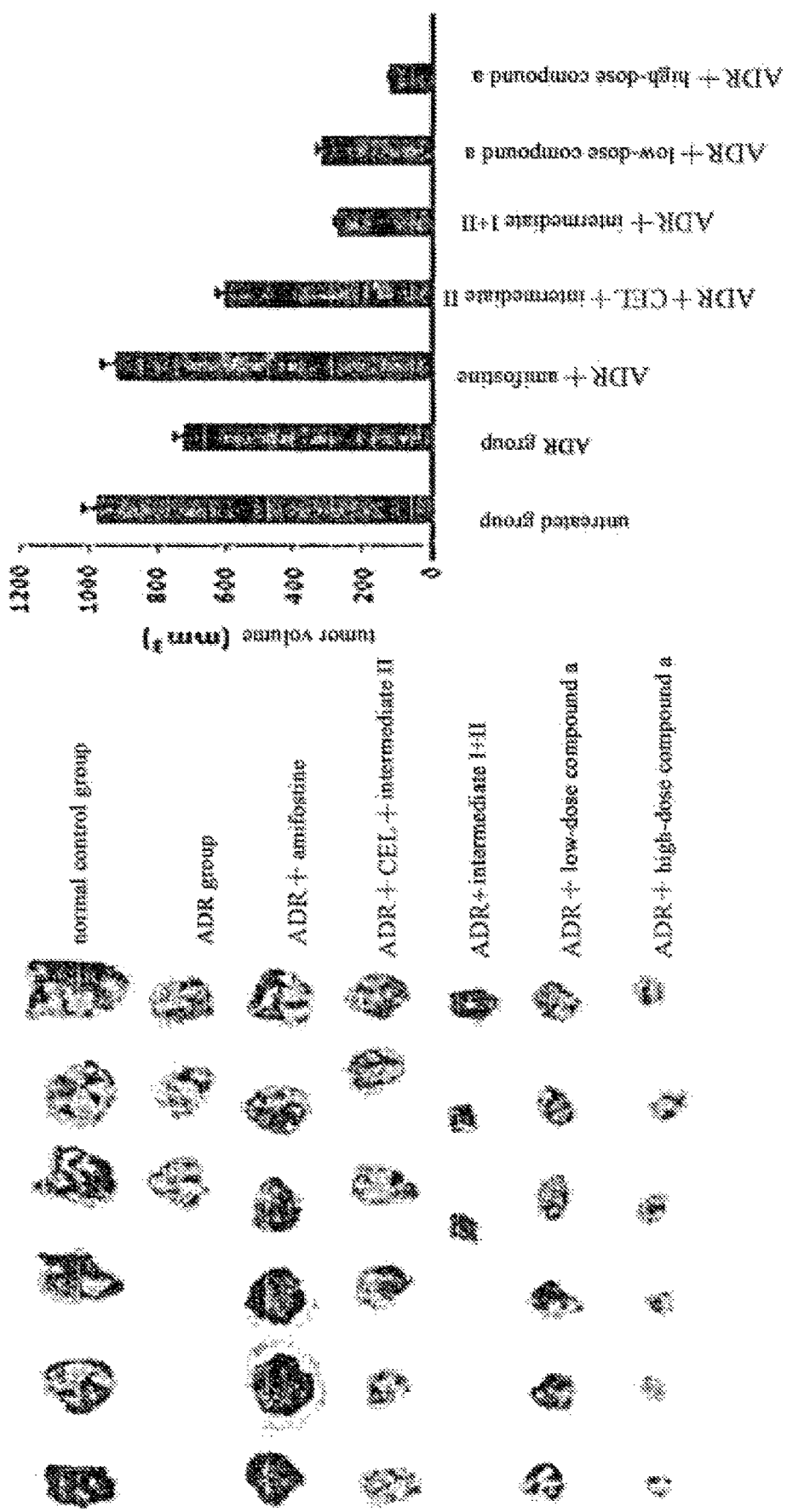
FIG. 9c shows the synergistic anti-tumor effect of the compounds of the present invention and chemotherapeutic agents.

The experiment was carried out using compound a in this example. Under sterile conditions, a suspension of colon cancer cells (SW480) in logarithmic growth phase (cell concentration was adjusted to 1×10$^7$/mL with physiological saline) was inoculated subcutaneously to 5 to 6 weeks old balb/c female nude mice on the right rear back, and each nude mice was inoculated at an amount of 0.3 ml, i.e. the number of cells contained was 3×10$^6$ per each mouse. 10 days later, subcutaneous transplanted tumor of 100-250 mm$^3$ appeared. The nude mice with tumor were randomly divided into several groups, each containing 6 mice: (1) control group; (2) doxorubicin group; (3) doxorubicin+amifostine; (4) doxorubicin+Celecoxib+intermediate II; (5) doxorubicin+intermediate I+intermediate II; (6) doxorubicin+low-dose compound a (6 mg/kg/day); (7) doxorubicin+high-dose compound a (15 mg/kg/day). Firstly, the following compounds were administered to each group of nude mice with tumor according to the following doses: intermediate I and intermediate II (3 mg/kg/day respectively), amifostine (400 mg/kg/day), Celecoxib (6 mg/kg/day). Except that amifostine was subcutaneously injected (30 minutes before irradiation), the other protective agents were administered by gavage. The above drugs were administered every day for 5 weeks continuously. 12 hours after the administration, doxorubicin (2.5 mg/kg) was injected intraperitoneally, and it was administered once every 2 days for 5 weeks. During the dosing period, the body weight of the nude mice was measured every two days with a precision electronic balance. The growth of the tumor and whether or not red and swelling and rupture occur were observed every day after inoculation. After tumor formation, the surface morphology and activity of the transplanted tumor were examined, and the longest diameter (a) and the shortest diameter (b) of the tumor nodules were measured every 3 days with a vernier caliper. Tumor volume was calculated according to the formula $V=0.5ab^2$, then the average value thereof was calculated, a tumor growth curve was plotted and tumor growth inhibition rate was calculated, wherein the tumor growth inhibition rate=(average volume of the control group−average volume of the irradiated group)/average volume of the control group×100%. 21 days after administration of doxorubicin, the tail vein blood of mice was collected to perform leukocyte count and blood biochemical index analysis. The results are summarized in Table 3. The tumor tissue and normal peripheral tissues were taken on the last day of treatment, and the content of the intermediate I therein was measured by HPLC (FIG. 9a). At the same time, paraffin sections were made, the occurrence of apoptosis was detected by terminal labeling (FIG. 9b), and the relative survival percentages of normal tissue and tumor tissue were calculated (the results are summarized in FIG. 9b). The volumes of tumor tissues in nude mice of each group are summarized in FIG. 9c. As can be seen from FIG. 9c, the administration of doxorubicin alone has a mild inhibitory effect on the tumor, and three mice die at the late stage of treatment and should be die of the side effect of doxorubicin, because mice that did not receive treatment by doxorubicin do not die. Compared with the known protective agent amifostine, compound a can significantly enhance the sensitivity of tumor cells to chemotherapy (p<0.001), resulting in the volume of tumor tissue being reduced significantly and dependent on dose. No death occurs in the treatment group, and more significant therapeutic effect was achieved. Although amifostine effectively protects the normal tissue, it significantly interferes with the inhibitory effect of doxorubicin on the tumor. More importantly, it can be seen from Table 3 and FIG. 9b that compound a is also effective in inhibiting the killing effect of Doxorubicin on normal leukocytes, cardiomyocytes and peripheral normal tissues around the tumor, which shows that the compound a of the present invention exhibits selectively inhibitory effect on tumor cells, i.e. the compound a only renders the tumor cells sensitive to Doxorubicin. However, the composition of intermediates I and II does not exhibit evident protective effect on leukocytes. The present invention first realizes that the content of active components in tumor tissues is evidently higher than that in the peripheral normal tissues, and provides experimental basis for selectively enhancing the sensitivity of the tumor cells to chemotherapeutic agents. In this study, the selective inhibitor against COX2, Celecoxib (CEL), was used as a control. The results show that the selective inhibitor against COX2 is significantly weaker than the compound of the present invention in the sensitizing effect on chemotherapeutic agents, and indicate that only when COX1 and COX2 are simultaneously inhibited, the excellent effect can be achieved. Using intermediate I alone can also enhance the sensitivity of the tumor to Doxorubicin, but the gastrointestinal side effects are extremely large, and the animals of the group die of gastrointestinal bleeding during the course of the treatment.

TABLE 3

Effect of compound a on the serological biochemical index of leukocytes

| Group | Number of nude mice | WBC ($\times 10^9$/L) | AST (μL) | CK-MB (μL) |
|---|---|---|---|---|
| control without administration | 6 | 8.2 ± 0.77 | 123 ± 12 | 329 ± 33 |
| Doxorubicin | 6 | 3.2 ± 0.31 | 382 ± 39 | 1282 ± 130 |
| Doxorubicin + amifostine[1] | 6 | 7.6 ± 0.67 | 198 ± 21 | 501 ± 52 |
| Doxorubicin + CEL + intermediate II[2] | 6 | 4.9 ± 0.51 | 302 ± 27 | 588 ± 60 |
| Doxorubicin + intermediates I + II[3] | 6 | 4.9 ± 0.42 | 712 ± 32 | 537 ± 59 |
| Doxorubicin + low-dose compound a[4] | 6 | 6.7 ± 0.59 | 239 ± 58 | 630 ± 56 |
| Doxorubicin + high-dose compound a[5] | 6 | 7.1 ± 0.72 | 203 ± 23 | 511 ± 55 |

Compared with the Doxorubicin group, [1]$P < 0.05$; [2]$P < 0.05$; [3]$P < 0.05$; [4]$P < 0.05$; [5]$P < 0.05$.

Example 11

Figure 10:
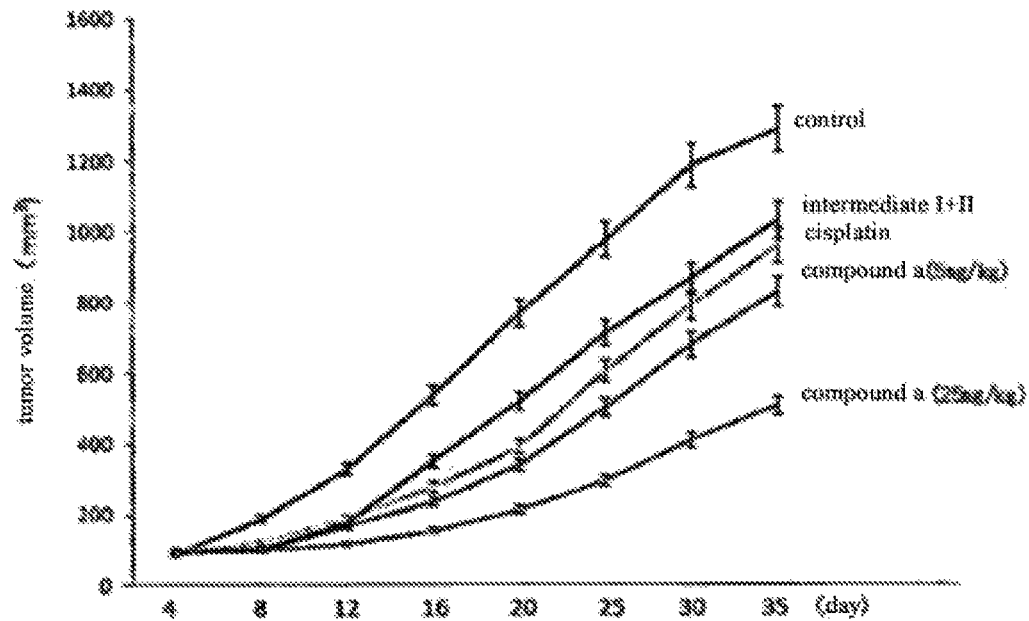
FIG. 10 shows the inhibitory effect of the compounds of the present invention used alone on tumors in nude mice.

Inhibitory effect of the compounds of the present invention used alone on transplanted tumors in nude mice An animal tumor model was constructed according to the manner and conditions described in Example 9, except that A549 cells were used instead of SW480 cells in Example 9, A549 cells were injected subcutaneously to the back and the outer side of the right hind leg of nude mice, and the nude mice with tumor were randomly divided into 5 groups (6 mice/group) randomly when the tumor volume reached 100-250 mm$^3$: (1) solvent (DMSO) control group; (2) intermediate I+II (12.5 mg/kg/day, respectively); (3) cisplatin (5 mg/kg/week); (4) low-dose compound a (5 mg/kg/day); (5) high-dose compound a (25 mg/kg/day). Except cisplatin (intraperitoneal injection, once a week), all compounds were administered by gavage, once a day for 5 weeks continuously. Body weight of animals and tumor volume were measured and calculated as described in Example 9. The tumor volume of each group is summarized in FIG. 10. It can be seen from the results that therapeutic dose of cisplatin has only mild inhibitory effect on the tumor, which is not as good as that of the low-dose compound a; compound a exhibits dose-dependent inhibitory effect against tumor; high-dose compound a inhibits 60% or more of tumors, and body weights of the animals were not significantly reduced during the administration (the results were not shown); inhibition against tumors caused by the corresponding high dose of the intermediates is weakened significantly, body weights of the animals decrease significantly at the late stage of treatment, and two animals die (the results are not shown). Thus, the compound of the present invention can be used as a single drug to effectively treat tumors.

Example 12

The synergistic inhibitory effect on tumors of the compounds of the present invention in combination with other anticancer agents.

Figure 11:
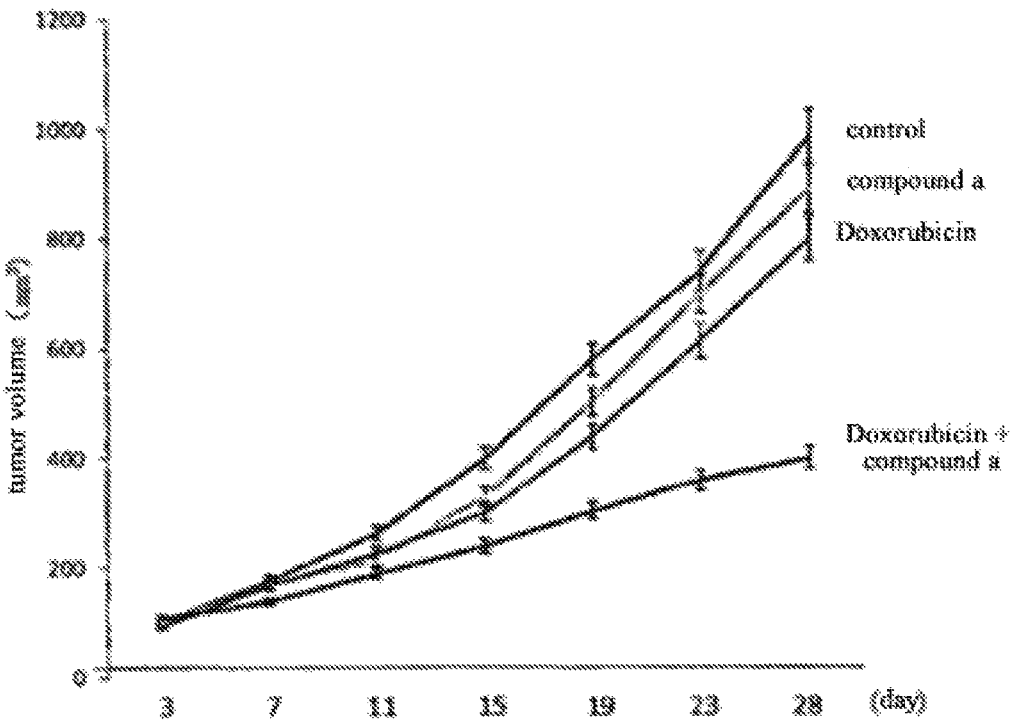
FIG. 11 shows that the compounds of the present invention, used in combination with doxorubicin, enhance the inhibitory effect of doxorubicin on tumors in nude mice.

The animal tumor model was constructed according to the manner and conditions described in Example 9 except that HT-29 cells were used instead of SW480 cells in Example 9, and the mice were randomly divided into 4 groups (6 mice/group) randomly when the tumor volume reached 100-250 mm$^3$: (1) solvent (DMSO) control group; (2) Doxorubicin (2 mg/kg/week); (3) Compound a (3 mg/kg/day); (4) compound a+Doxorubicin (3 mg/kg/day and 2 mg/kg/week, respectively). Compound a was administered by gavage once a day for 4 weeks continuously; Doxorubicin was injected intraperitoneally once a week for 4 weeks. Body weight and tumor volume of animals were measured and calculated according to Example 9. The tumor volumes of nude mice in each group are summarized in FIG. 11. As can be seen from FIG. 11, when the low dose of doxorubicin or compound a is administered alone, the tumor is only slightly inhibited; when the two compounds are used in combination, up to 60% of the tumor is inhibited, and the body weights of the animals increase by about 10% (the results are not shown). This indicates that use of the preparation of the present invention in combination with other preparations commonly used in the treatment of cancer greatly improves the therapeutic effect on tumors.

In summary, the project of the present invention exhibits unexpected selectivity, and really realizes significantly enhancing the sensitivity of tumor tissues to radiotherapy and chemotherapy while reducing the side effects of radiotherapy and chemotherapy. Thus, the two major bottlenecks in cancer treatment, i.e. side effects and tolerance, are solved simultaneously to a large extent. In addition, the present invention has also developed a novel anti-cancer drug which achieves excellent tumor inhibiting effect when used alone and has no obvious toxic and side effect.

The invention claimed is:

1. A compound as shown by formula 1:

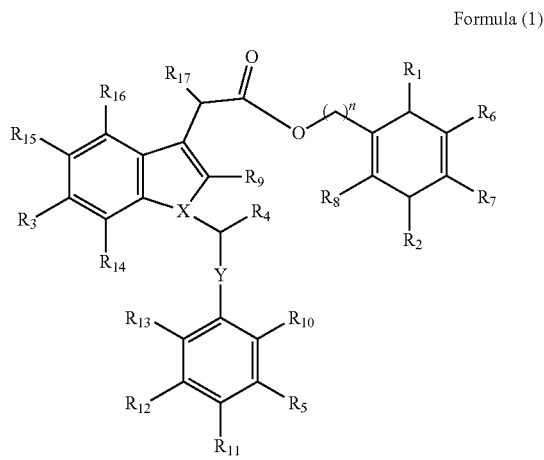

Formula (1)

wherein, the groups $R_1$ to $R_{17}$ are each independently selected from the group consisting of hydrogen, fluorine, chlorine, bromine, iodine, $C_1$-$C_8$ alkyl, $C_1$-$C_8$ alkoxy, oxo(=O), carbonyl, hydroxyl, amino, azido, carboxyl and $C_1$-$C_8$ alkylsulfinyl; X is a nitrogen atom; Y is selected from the group consisting of single bond, $C_1$-$C_8$ alkylene, $C_6$-$C_{20}$ arylene and $C_4$-$C_{20}$ heteroarylene; and n is an integer from 5 to 20, and a pharmaceutically acceptable salt thereof.

2. The compound according to claim 1, characterized in that the groups $R_1$ to $R_4$ are each independently selected from the group consisting of hydrogen, fluorine, chlorine, $C_1$-$C_4$ alkyl, $C_1$-$C_4$ alkoxy, carbonyl, oxo(=O), and hydroxyl; $R_{11}$ is selected from the group consisting of hydrogen, fluorine, chlorine, bromine, iodine, azido and $C_1$-$C_3$ alkylsulfinyl; $R_6$ to $R_9$ are each independently selected from hydrogen, $C_1$-$C_4$ alkyl and $C_1$-$C_4$ alkoxy; $R_5$, $R_{10}$, $R_{12}$ to $R_{17}$ are each independently selected from hydrogen, $C_1$-$C_4$ alkyl, $C_1$-$C_4$ alkoxy and amino; X is a nitrogen atom; Y is selected from the group consisting of single bond, $C_1$-$C_6$ alkylene, $C_6$-$C_{15}$ arylene and $C_4$-$C_{15}$ heteroarylene; and n is an integer of 5 to 20.

3. The compound according to claim 1, characterized in that the compound is selected from the compounds shown by any of the following formulae a, b, e and f, and pharmaceutically acceptable salts thereof:

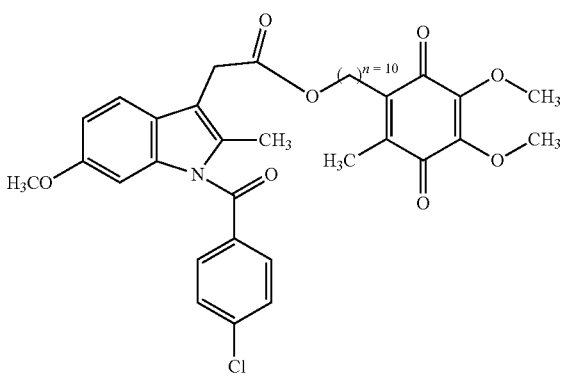

a

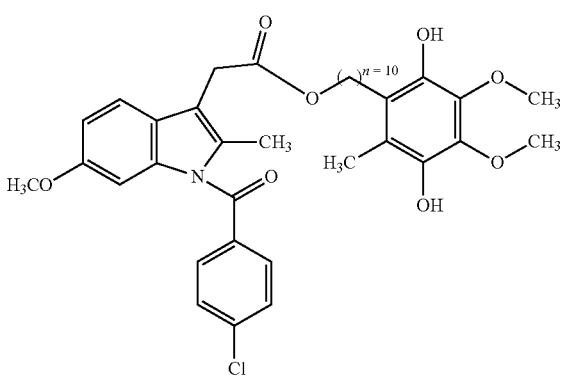

b

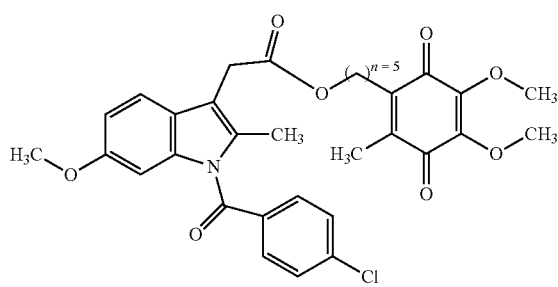

e

-continued

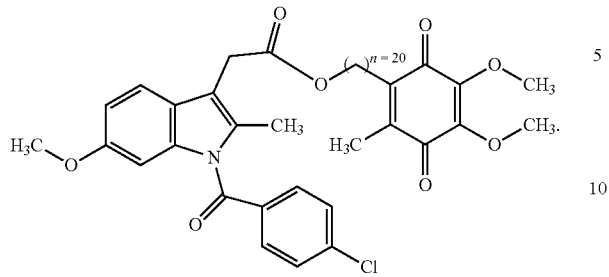

f

5

10

4. A pharmaceutical composition, comprising:
(i) the compound according to claim 1 or a pharmaceutically acceptable salt prodrug thereof;
(ii) optionally one or more of pharmaceutically acceptable fillers, carriers and diluents; and
(iii) optionally a pharmaceutically active component different from the component (i) selected from one or more of the following substances: uramastine, amifostine, chlorambucil, mustine, cyclophosphamide, paclitaxel, Thiotepa, cisplatin, busulfan, doxorubicin, carmustine 5-fluorouracil, celecoxib, mercaptopurine, methotrexate, tegafur, gefitinib, hydroxyurea, cytosine arabinoside, carboplatin, Iproplatin, prednisone, prednisolone, dexamethasone, diethylstilbestrol, estradiol, raloxifene, Testosterone propionate, semustine, lomustine, thioguanine, etoposide, vincristine, ifosfamide, Navelbine, gemcitabine, mitomycin and vindesine.

* * * * *